(12) United States Patent
Thuring et al.

(10) Patent No.: US 8,497,270 B2
(45) Date of Patent: Jul. 30, 2013

(54) MACROCYCLIC INTEGRASE INHIBITORS

(75) Inventors: Johannes Wilhelmus J Thuring, Antwerp (BE); Jean-Francois Bonfanti, Ande (FR); Jerome Michel Claude Fortin, Igoville (FR)

(73) Assignee: Elanco Animal Health Ireland Limited, Indianapolis, IN (US)

( * ) Notice: Subject to any disclaimer, the term of this patent is extended or adjusted under 35 U.S.C. 154(b) by 17 days.

(21) Appl. No.: 13/395,891

(22) PCT Filed: Oct. 13, 2010

(86) PCT No.: PCT/EP2010/065300
§ 371 (c)(1),
(2), (4) Date: Mar. 14, 2012

(87) PCT Pub. No.: WO2011/045330
PCT Pub. Date: Apr. 21, 2011

(65) Prior Publication Data
US 2012/0172367 A1    Jul. 5, 2012

(30) Foreign Application Priority Data

Oct. 13, 2009 (EP) .................................... 09172853

(51) Int. Cl.
| C07D 471/18 | (2006.01) |
| C07D 498/18 | (2006.01) |
| C07D 513/18 | (2006.01) |
| C07D 515/18 | (2006.01) |
| C07D 498/22 | (2006.01) |
| A61K 31/547 | (2006.01) |
| A61P 31/18 | (2006.01) |

(52) U.S. Cl.
USPC ............ 514/250; 514/286; 540/456; 540/460

(58) Field of Classification Search
USPC .......................... 540/456, 460; 514/250, 286
See application file for complete search history.

(56) References Cited

FOREIGN PATENT DOCUMENTS
WO        02/30931        4/2002

*Primary Examiner* — Bruck Kifle
(74) *Attorney, Agent, or Firm* — James J. Sales

(57) ABSTRACT

Compound having formula (I), wherein —W is NH—, —N(CH$_3$)— or piperazine, —X is a bond, —C(=O)— or S(=O)$_2$—, —Y is C$_{3-7}$alkylene, and —Z is NH—C(=O)— or —O—, and pharmaceutically acceptable salts thereof, their pharmaceutical formulations and use as HIV inhibitors.

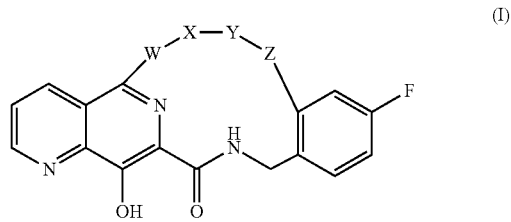

(I)

15 Claims, No Drawings

MACROCYCLIC INTEGRASE INHIBITORS

CROSS-REFERENCE TO RELATED APPLICATIONS

This application is a national phase application under 35 U.S.C. 371 of, and claims priority to, PCT Application No. PCT/EP2010/065300, filed 13 Oct. 2010, which claims the priority benefit of European patent application 09172853.5 filed 13 Oct. 2009.

This invention concerns naphthyridin derivatives having HIV (Human Immunodeficiency Virus) replication inhibiting properties, the preparation thereof and pharmaceutical compositions comprising these compounds.

Initially, treatment of HIV infection consisted of monotherapy with nucleoside derivatives and although successful in suppressing viral replication, these drugs quickly lost their effectiveness due to the emergence of drug-resistant strains. It became clear that a high mutation rate combined with rapid replication made HIV a particularly challenging target for antiviral therapy. The introduction of combination therapy of several anti-HIV agents improved therapeutic outcome. The current standard of care is the so-called HAART (Highly Active Anti-Retroviral Therapy), which offers a powerful and sustained viral suppression. HAART typically involves a combination of nucleoside or nucleotide reverse transcriptase inhibitors (NRTIs or NtRTIs respectively) with a non-nucleoside reverse transcriptase inhibitor (NNRTI), a protease inhibitor (PI), and an integrase inhibitor or entry inhibitor. Current guidelines for antiretroviral therapy recommend at least a triple combination therapy regimen even for initial treatment. Although HAART is capable of suppressing HIV up to undetectable levels, resistance can emerge due to compliance problems. It also has been shown that resistant virus is carried over to newly infected individuals, resulting in severely limited therapy options for these drug-naive patients.

Therefore there is a continued need for new and effective compounds that can be used as anti-HIV drugs. In particular, there is need for further HIV integrase inhibitors that are more effective in terms of activity against wild type virus, but also against mutated strains, in particular toward mutated strains selected by the currently approved or nearly approved integrase inhibitors such as raltegravir and elvitegravir. Primary mutations most frequently developed during raltegravir therapy include N155H and Q148K/R/H, and infrequently Y143R/C. The acquisition of N155 or Q148 mutations was found to result in cross-resistance to structurally diverse integrase inhibitors.

There is a need for integrase inhibitors that offer advantages in terms of their pharmacokinetic and/or pharmacodynamic profile, in particular that are devoid of extensive protein binding. Other aspects that should be considered in the development of further integrase inhibitors include a favorable safety prophile, dosing and/or the lack of the need for boosting.

Other HIV integrase inhibitors are known in the art. For instance, WO0255079, WO0230931, WO0230930 and WO0230426 (all by Merck & Co., Inc.) disclose aza- and polyaza-naphthalenyl carboxamides useful as inhibitors of HIV integrase. WO0236734 (by Merck & Co., Inc.) discloses additionally aza- and polyaza-naphthalenyl ketones useful as inhibitors of HIV integrase. In Roggo et al., Journal of antibiotics (1996), spirodihydrobenzofuranlactams are disclosed as antagonists of endothelin and as inhibitors of HIV-1 protease.

EP0459449 by Shionogi & Co., discloses furano[2,3-F] isoindoles as aldose reductase inhibitors. CS225002 (by Krepelka Jiri and Vlckova Drahuse) discloses 9-phenyl-1H-benzo[f]isoindole-1,3-dione derivatives capable of inhibiting tumors in mice and rats. Similarly, CS210880 (by Krepelka Jiri, Vancurova Iva and Roubik Jiri) discloses certain 4-aryl-naphthalene-2,3-dicarboxylic acid imides as antineoplastic active compounds. The article by Krepelka et al., Collect. Czech. Chem. Commun. (1982), 47(1), pp 304-14 discloses the synthesis and neoplastic effects of some N-substituted imides of 1-substituted 4-arylnaphthalene-2,3-dicarboxylic acids. Polycyclic carbamoylpyridones have also been disclosed as inhibitors of HIV integrase in EP1874117 by Smithkline Beecham Corp. and Shionogi. WO2005118593 from Bristol Myers Squibb discloses a series of bicyclic heterocycles as integrase inhibitors, and WO2004103278 discloses a series of acyl sulfonamides as inhibitors of Hiv integrase. Gilead Sciences Inc. disclosed a series of aza-quiniolinol phosphonate compounds as integrase inhibitors in WO2005028478 and a series of pre-organised tricyclic integrase inhibitors in WO2004035577. Furthermore, a series of pyridopyrazine and pyrimidopyrazine-dione compounds was disclosed by Instituto di Ricerche di Biologia Moleculare p Angeletti Spa in WO2005087766. Additioanlly, tetrandyro-4H-pyrido (1,2-a) pyrimidines and related compounds were disclosed byt Instituto di Ricerche di Biologia Moleculare p Angeletti Spa in WO2004058757. Japan Tobacco Inc have disclosed 4-oxyquinoline compounds as HIV integrase inhibitors in WO2004046115, and a 6-(heterocycle-substituted benzyl)-4-oxoquinoline compound as an HIV inhibitor in US20080207618.

The present invention is aimed at providing particular novel series of naphthyridine derivatives having HIV integrase and HIV replication inhibiting properties.

The compounds of the invention differ from prior art compounds in structure, antiviral activity and/or pharmacological potency. It has been found that they not only are very active against wild type virus, but also against mutant strains, in particular against strains that display resistance to one or more known integrase inhibitors, which strains are referred to as drug- or multidrug-resistant HIV strains.

Thus, in one aspect, the present invention concerns compounds of formula I, including the stereo chemically isomeric forms thereof, which can be represented by formula I:

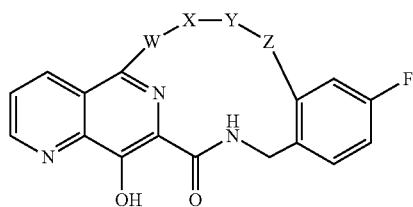

and,
wherein
W is —NH—, —N(CH$_3$)— or piperazine,
X is a bond, —C(=O)— or —S(=O)$_2$—,
Y is C$_{3-7}$alkylene,
Z is —NH—C(=O)— or —O—, and,
pharmaceutically acceptable salts thereof.

Whenever used in a molecular fragment or group, a dashed line - - - represents the bond linking that fragment or group with the remainder of the molecule.

As used herein C$_{3-7}$alkylene as a group or part of a group defines straight or branched bivalent chain saturated hydrocarbon radicals having from 3 to 7 carbon atoms such as propylene, 2-propyl, 1-butylene, propylene, hexylene or heptylene. Of interest among $C_{3-7}$alkylene is $C_{4-5}$alkylene or $C_{3-4}$alkylene; $C_{4-5}$alkylene defines straight or branched bivalent chain saturated hydrocarbon radicals having from 4 or 5 carbon atoms; $C_{3-4}$alkylene defines straight or branched bivalent chain saturated hydrocarbon radicals having from 3 or 4 carbon atoms. Of interest are those alkylene radicals being straight.

Whenever a radical occurs in the definition of the compounds of formula (I) or in any of the subgroups specified herein, said radical independently is as specified above in the definition of the compounds of formulas (I) or in the more restricted definitions as specified hereinafter.

It should also be noted that the radical positions on any molecular moiety used in the definitions may be anywhere on such moiety as long as it is chemically stable. For instance butyl includes 1-butyl and 2-butyl.

Some of the compounds of formula (I) may also exist in their tautomeric form. Such forms although not explicitly indicated in the above formula are intended to be included within the scope of the present invention.

The present invention is also intended to include any isotopes of atoms present in the compounds of the invention. For example, isotopes of hydrogen include tritium and deuterium and isotopes of carbon include C-13 and C-14.

Whenever used hereinabove or hereinafter, the terms "compounds of formula (I)", "the present compounds", "the compounds of the present invention" or any equivalent terms, and similarly, the terms "subgroups of compounds of formula (I)", "subgroups of the present compounds", "subgroups of the compounds of the present invention" or any equivalent terms, are meant to include the compounds of general formula (I), or subgroups of the compounds of general formula (I), as well as their salts, solvates, and stereoisomers.

When any variable occurs more than once in any moiety, each definition is independent. Any limited definitions of the radicals specified herein are meant to be applicable to the group of compounds of formula (I) as well as to any subgroup defined or mentioned herein.

Subgroups of compounds of formula I are those compounds of formula I, or subgroups of compounds of formula I, as defined herein,
wherein W is —NH— or —N(CH$_3$)—, or,
wherein X is a bond or —S(═O)$_2$—, or,
wherein Y is $C_{4-5}$alkylene, or,
wherein X is —C(═O)— and Y is $C_{3-4}$alkyl when W is piperazine, or,
wherein Z is —O—, or,
wherein Z is —NH—C(═O)—, in particular wherein the nitrogen of —NH—C(═O)— is connected to Y, or
wherein the —W—X—Y—Z— linker is 8 or 9 atoms long, or,
wherein —W—X—Y—Z— is selected from:
- - -NH—C$_{5-7}$alkylene-NH—C(═O)- - -,
- - -N(CH$_3$)—S(═O)$_2$—C$_{4-5}$alkylene-NH—C(═O)- - -,
- - -N(CH$_3$)—S(═O)$_2$—C$_{4-5}$alkylene-O- - -,

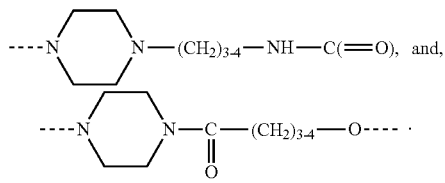

The pharmaceutically acceptable addition salt forms, which the compounds of the present invention are able to form, can conveniently be prepared using the appropriate acids, such as, for example, inorganic acids such as hydrohalic acids, e.g. hydrochloric or hydrobromic acid, sulfuric, hemisulphuric, nitric, phosphoric, and the like acids; or organic acids such as, for example, methanesulfonic, ethanesulfonic, benzenesulfonic, p-toluenesulfonic, and the like acids. Conversely said acid addition salt forms can be converted into the free base form by treatment with an appropriate base.

The compounds of formula (I) containing acidic protons may be converted into their pharmaceutically acceptable metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary, and tertiary aliphatic and aromatic amines such as methylamine, ethylamine, propylamine, isopropylamine, the four butylamine isomers, dimethyl-amine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

Preparation of the Compounds

A compound according to the invention can generally be prepared by a succession of steps, each of which is known to the skilled person. In particular, the compounds in this patent application can be prepared according to one or more of the following preparation methods. In the following schemes, and unless otherwise indicated, all variables used are as defined for compounds of Formula (I).

The macrocycles with the general formula (I) of the present invention can be prepared through a cyclization reaction involving an "open" precursor of the general formula (II), in which the 8-hydroxyl function of the 1,6-naphthyridine is protected with a protecting group (PG), or, alternatively, is kept unprotected and used as the free hydroxyl function. Examples of suitable protecting groups for said hydroxyl function are, $C_{1-4}$alkyl, benzyl, aryl sulfonyl, and benzoyl. Said cyclization can be effected through the formation an amide bond, involving the carboxylic acid function at the 7-position of the naphthyridine scaffold, as is shown in Scheme 1, and requires the presence of a dehydrating reagent. Commonly used examples are HBTU (O-benzo-triazole-N,N,N',N'-tetramethyl uronium hexafluorophosphate), EDCI (1-ethyl-3-(3-di-methylaminopropyl)carbodiimide)(1-ethyl-3-(3-dimethylaminopropyl)carbodiimide), EDAC (1-ethyl-3-(3-dimethylaminopropyl) carbodiimide hydrochloride), or FDPP (pentafluorophenyl diphenylphosphinate). In a particular embodiment said dehydrating reagent is HBTU or FDPP. The reaction is typically performed by slow addition of the open precursor of the general formula (II) to a mixture containing said dehydrating agent and an excess amount of a tertiary amine, such as diisopropyl ethyl amine, or the like. A useful solvent is an aprotic solvent like CH$_2$Cl$_2$, or more preferably a polar aprotic solvent like DMF. Under certain circumstances the use of HOBT (hydroxybenzotriazole) as an additive is an advantage. In a preferred embodiment the cyclization reaction is carried out at low concentration of the open precursor (II), such as in the range between 1 and 10 mM, in particular at 4 mM.

In another embodiment, the macro cyclization reaction can be effected in the linker region —W—X—Y—Z—, for example in the preparation of compounds of formula I wherein Z represents an amide bond of formula —NH—C (=O)— wherein intermediate of formula IIa is cyclized using a methodology as described hereinbefore to form a macrocyclic amide bond.

The deprotection of the 8-hydroxyl group of compounds of formula III as illustrated in Scheme 1 can be affected using various conditions, and depends on the particular protecting group PG. In one embodiment, when PG is benzyl, a macrocycle of the general formula (III) can be treated with trifluoro acetic acid at a temperature between 0° C. and 80° C. Optionally, an aprotic co-solvent such as dichloro methane can be advantageously used. It might also be advantageous to apply an agent that traps the resulting benzylic carbocation, for example triisopropyl silane, or the like. In a second embodiment, when PG is Me, the macrocycle of the general formula (III) can be treated with sodium iodide and tetrachloro silane in a solvent mixture consisting of a polar aprotic solvent, such as acetonitrile or the like, and an aromatic apolar solvent, such as toluene or the like. Said transformation is advantageously carried out in a temperature range between 0° C. and room temperature. Alternatively, said deprotection is carried out using a boron reagent, such as boron tribromide ($BBr_3$), in an aprotic solvent such as dichloro methane, or the like, at low temperature, such as at −78° C. In a third embodiment, when PG is para tolyl sulfonyl, a macrocycle of the general formula (III) can be treated with a sodium alkoxide in the corresponding alcoholic solvent, eg sodium methoxide in methanol, at room temperature. Optionally a polar aprotic co-solvent can be applied, such as DMF, or the like.

The compounds of formula II are obtained from compounds of formula IV, and compounds of formula IIa from compounds of formula VI, by using appropriate deprotection methods as described for and illustrated by Scheme 2 and Scheme 2a respectively.

Various methods to obtain (subgroups) of intermediate compounds of formulas IV or VI starting from a compound of formula XI are described for and illustrated by schemes 3, 4, 4a, 4b, 4c, 5a, 5b and 5c.

The naphthyridine of the general formula (XI) can be prepared with different protecting groups (PG). The choice of PG depends on the particular functional groups A, B, C and D, as defined hereinbefore. The PG is installed on the hydroxyl napththyridine of the general formula (XIa), as is shown in Scheme 1. When PG is benzyl or $C_{1-4}$alkyl, said naphtyridine (XIa) is treated with an inorganic base, such as cesium carbonate or the like, in a polar, aprotic solvent, such as DMF, or the like, followed by addition of a $C_{1-4}$alkyl halide, such as methyl iodide, or benzyl bromide to afford the intermediate of the general formula (XI). The reaction is most advantageously carried out at room temperature. Alternatively, when PG=para tolyl sulfonyl, said naphtyridine (XIa) is treated with para toluene sulfonyl chloride, in the presence of a tertiary amine base, such as triethyl amine, or the like. A suitable solvent is a chlorinated hydrocarbon, such as chloroform, or the like, and the reaction temperature should be between 20° C. and 50° C.

Scheme 1

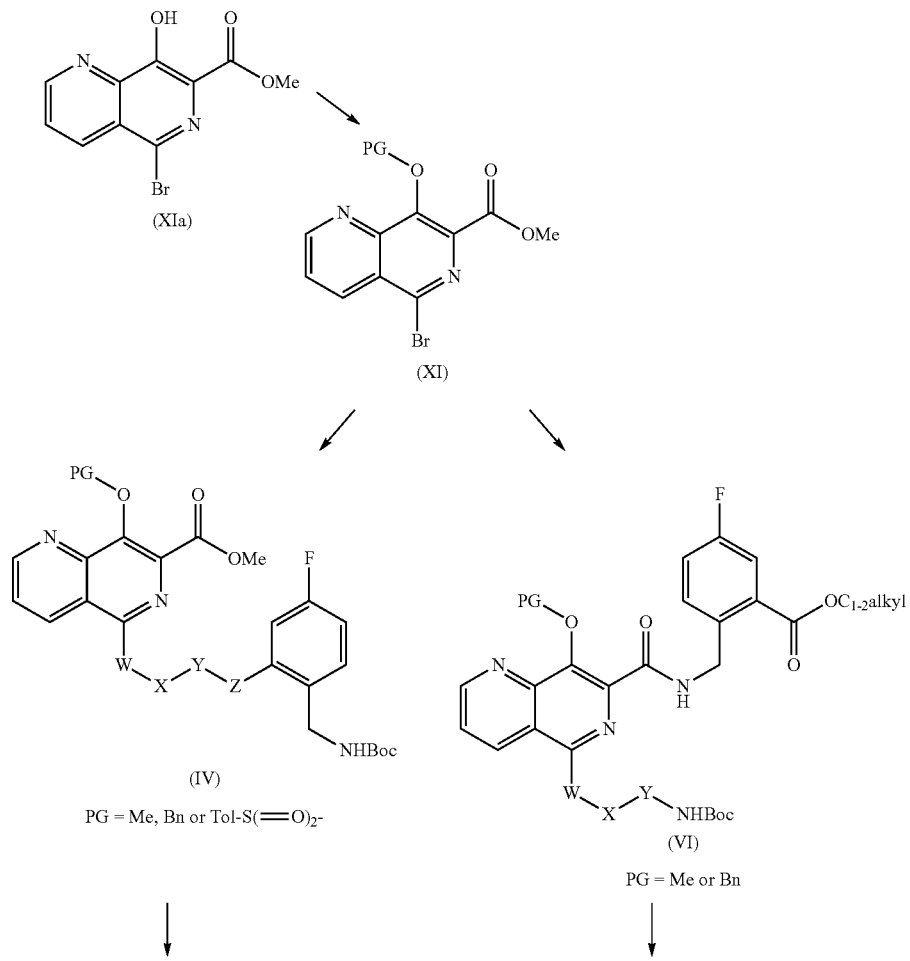

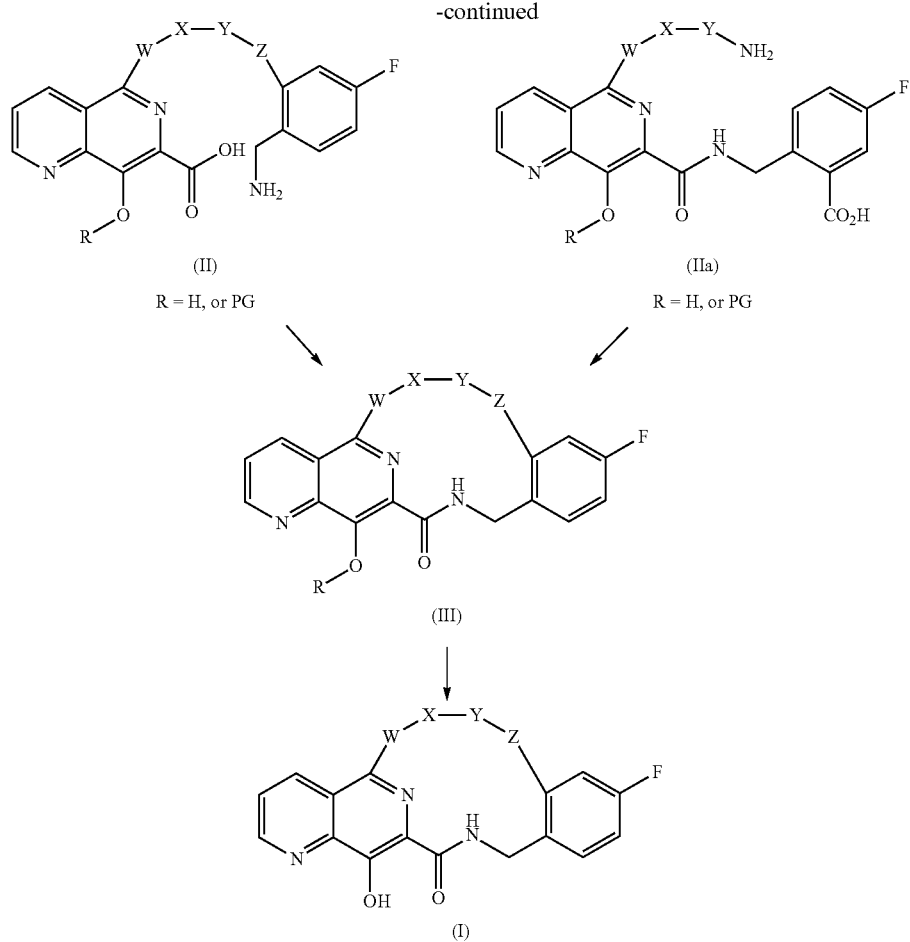

The open precursors of the general formula (II) can be prepared in two steps starting from the protected precursor of the general formula (IV), as is shown in Scheme 2: First, the carboxylic ester of the general formula (IV) is saponified to yield the corresponding carboxylic acid of the general formula (V). This transformation can be effected by using a metal hydroxide (M-OH), such as potassium hydroxide, sodium hydroxide, or lithium hydroxide. The reaction is performed in an aqueous environment, and is most advantageously carried out in the presence of at least one water miscible organic co-solvent, such as methanol, ethanol or THF, or the like. In a second step, the amine Boc protecting group was removed to afford the macrocyle precursor of the general formula (II). This can be achieved by treating the Boc intermediate of formula (V) with a solution containing trifluoro acetic acid, optionally in the presence of triisopropyl silane, in an aprotic solvent, such as dichloro methane, or the like. In a preferred embodiment, said transformation is carried out between 0° C. and room temperature. Alternatively, said deprotection can be effected by treatment of (V) with a solution of hydrochloric acid in a polar, aprotic solevent, such as dioxane, in particular with a 4N solution of HCl in dioxane.

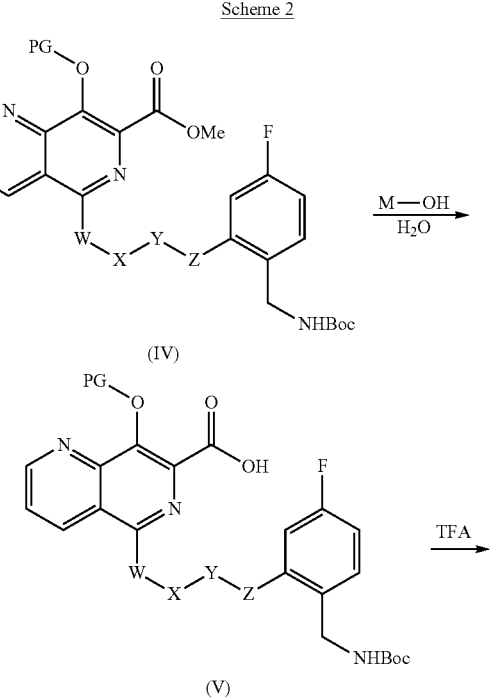

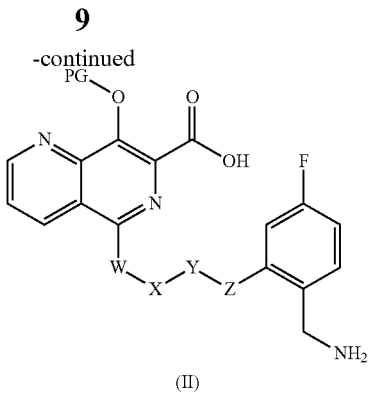

(II)

PG = Me, Bn or Tol-S(=O)₂-

The open precursors of the general formula (IIa) can be prepared in two steps starting from the protected precursor of the general formula (VI), as is shown in Scheme 2a:

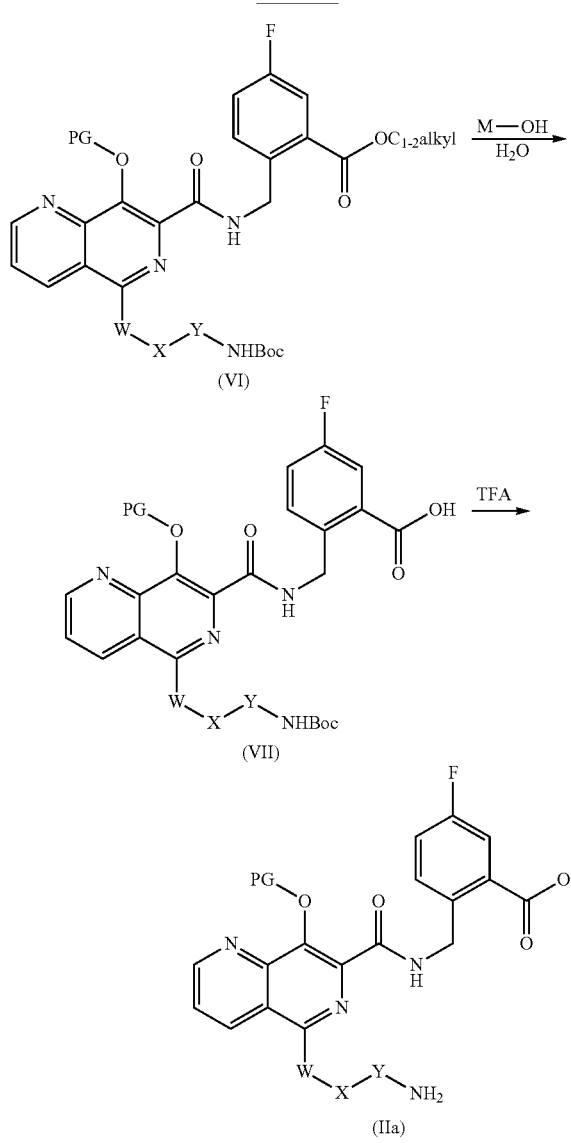

PG = Me or Bn

First, the carboxylic ester of the general formula (VI) is saponified to yield the corresponding carboxylic acid of the general formula (VII). This transformation can be effected by using a metal hydroxide (M-OH), such as potassium hydroxide, sodium hydroxide, or lithium hydroxide. The reaction is performed in an aqueous environment, and is most advantageously carried out in the presence of at least one water miscible organic co-solvent, such as methanol, ethanol or THF, or the like. In a second step, the amine Boc protecting group was removed to afford the macrocyle precursor of the general formula (IIa). This can be achieved by treating the Boc intermediate of formula (VII) with a solution containing trifluoro acetic acid, optionally in the presence of triisopropyl silane, in an aprotic solvent, such as dichloro methane, or the like. In a preferred embodiment, said transformation is carried out between 0° C. and room temperature.

The precursor of the general formula (VI) can be prepared in two steps from the naphthyridine of the general formula (VIII), as is depicted in Scheme 3. The first step involves the saponification of intermediate (VIII), which can be carried out by reaction with a metal hydroxide (M-OH), such as potassium hydroxide, or sodium hydroxide. The reaction is performed in an aqueous environment, and is most advantageously carried out in the presence of at least one water miscible organic co-solvent, such as methanol, or the like. Further conversion of the carboxylic acid (IX) into the amides of formula (VI) is done using art known procedures, such as the treatment with the hydrochloric acid salt of the primary amine of the formula (X), such as methyl 2-(aminomethyl)-5-fluorobenzoate hydrochloride when $C_{1-2}$alkyl is methyl, in the presence of a conventional amide coupling reagent such as HBTU (O-benzotriazole-N,N,N',N'-tetramethyl uronium hexafluorophosphate), EDCI (1-ethyl-3-(3-dimethyl-aminopropyl)carbodiimide), or EDAC (1-ethyl-3-(3-dimethylaminopropyl) carbodiimide hydrochloride) in an aprotic solvent like $CH_2Cl_2$, in the presence of an amine base additive, such as diisopropyl ethyl amine. Under certain circumstances the use of HOBT (hydroxybenzotriazole) as an additive is an advantage.

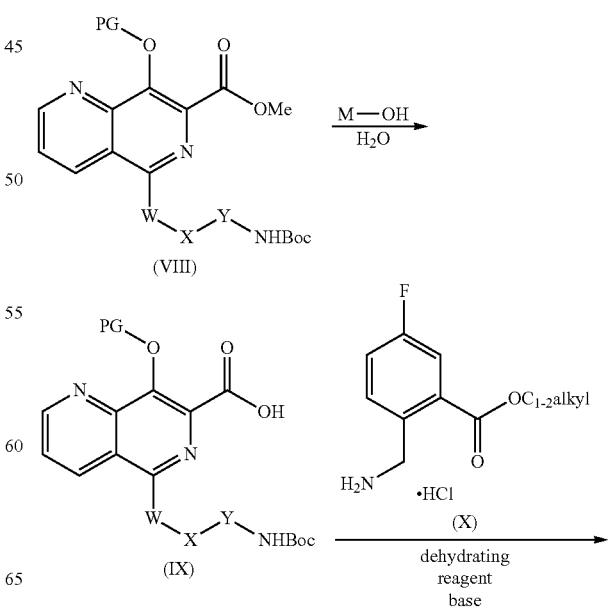

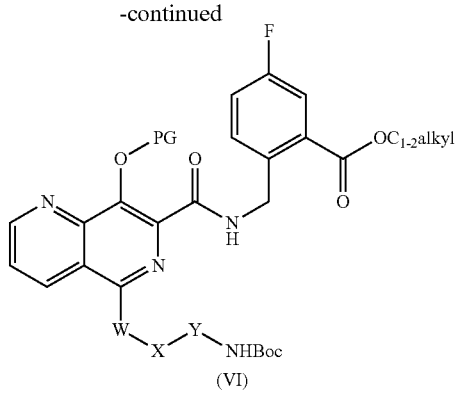

(VI)

PG = Me or Bn

The intermediate of the general formula (VIIIf) can be prepared in several ways, depending on the nature of the functional groups W and X, as defined hereinbefore. In a first embodiment, when W is —NH—, and X is a bond, the reaction as shown in Scheme 4 can be used. Suitable protecting groups (PG) in this reaction are Me and Bn. Said transformation involves the use of a mono-protected bis-amine linker (XII). More particularly, said protecting group is a Boc group. Said linker can be introduced by treating a mixture of the bromide (XI) and a tertiary amine, such as diisopropyl ethyl amine, or the like, in a polar, aprotic solvent, such as DMA, with the amine (XII). The reaction is most advantageously carried out in a temperature range 80-160° C., in particular at 140° C., to afford the carboxylic ester of the general formula (VIIIf).

Scheme 4

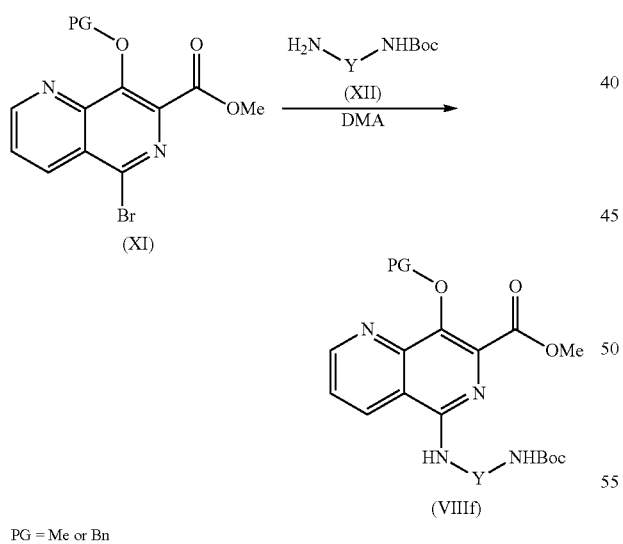

(VIIIf)

PG = Me or Bn

In a second embodiment, when W is piperazinyl, and X is a bond, the sequence as shown in Scheme 4a can be followed. In a first step, piperazine is incorporated in the naphthyridine of the general formula (XI). This can be done by treating a mixture of the bromide (XI) and a tertiary amine, such as diisopropyl ethyl amine, or the like, in a polar, aprotic solvent, such as DMA, with piperazine. The reaction is most advantageously carried out in a temperature range 80-140° C., in particular at 110° C., to afford the piperazine of the general formula (XIII). In a second step, said piperazine (XIII) is treated with a bromo containing linker of the general formula (XIV). For example, when Y is $C_4$alkyl, said linker is tent-butyl 4-bromobutylcarbamate. This transformation requires the presence of an inorganic base, such as potassium carbonate, or the like. The reaction is advantageously carried out in a polar aprotic solvent, such as DMA, or the like, and affords the naphthyridine of the general formula (VIIIa).

Scheme 4a

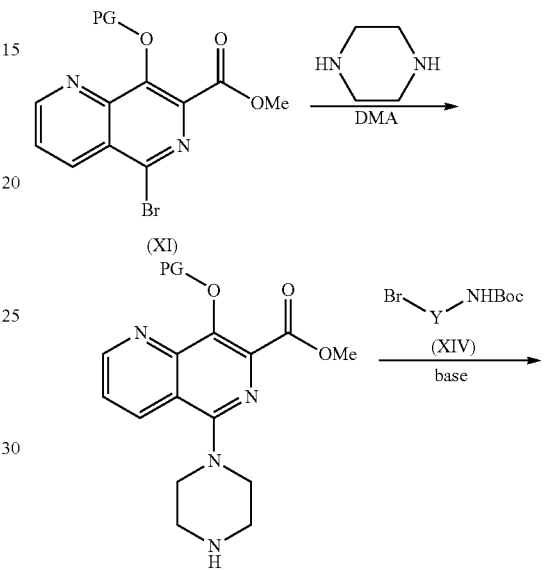

(XIII)

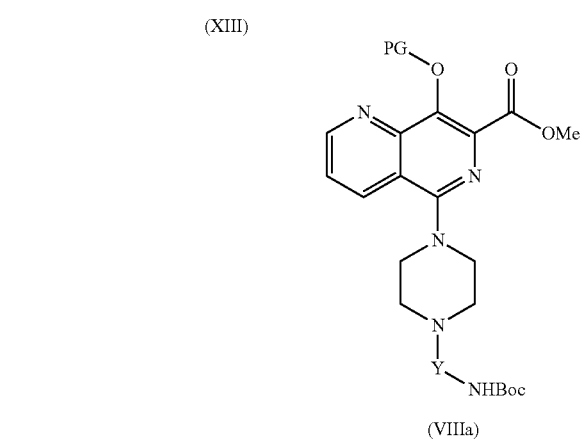

(VIIIa)

PG = Me or Bn

In a third embodiment, when W is —N($CH_3$)—, X is —S(=O)$_2$—, Y is $C_{3-7}$alkylene, and Z is —NH—C(=O)—, the reaction as described in Scheme 4b can be followed, using the protected bromo naphthyridine of the general formula (XI). Suitable protecting groups are methyl or tosyl. The functionalized naphthyridine of the general formula (VIIIb) is prepared by reacting the bromo naphthyridine (XI) with the protected amino functionalized linker of the general formula (XV). The use of a copper(I) base, such as copper(I) oxide, in the presence of a ligand, such as 2,2'-bipyridine offer advantages in this reaction. Useful solvents are polar, aprotic solvents, such as DMA, NMP, or the like. The reaction needs elevated temperatures, typically in the range between 80° C. and 140° C., in particular 120° C.

Scheme 4b

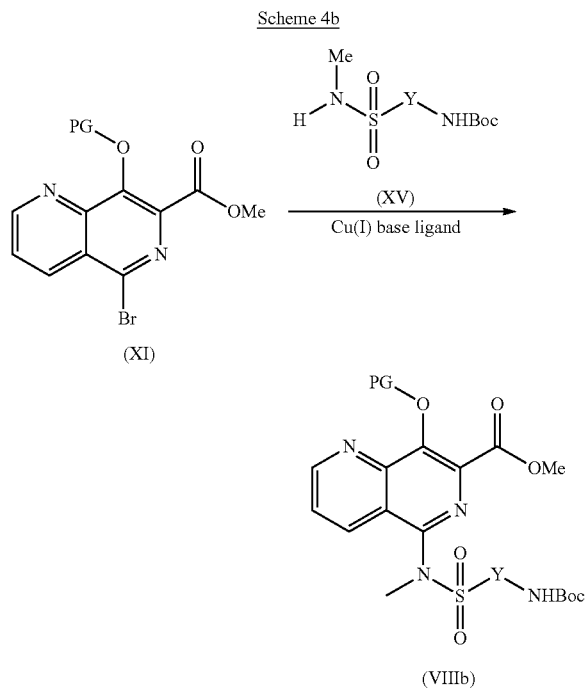

PG = Me or -S(=O)₂-Tol

In certain cases it is advantageous to carry out a protecting group (PG) transformation of the 8-hydroxy function of the naphthyridine. An example of such is a strategy is the interconversion of the tosyl group in (VIIIc) into a benzyl group in (VIIIe), as is shown in Scheme 4c. The deprotection step involves treatment of the tosylate (VIIIc) with a sodium alkoxide in the corresponding alcoholic solvent, eg sodium methoxide in methanol. The reaction temperature is between 20 and 60° C. Optionally a polar aprotic co-solvent can be applied, such as DMF, or the like. The re-protection to afford the benzyl oxy napthhyridine of the general formula (VIIIe) can be performed by treating (VIIId) with an inorganic base, such as cesium carbonate or the like, in a polar, aprotic solvent, such as DMF, or the like, followed by addition of a benzyl halide, such as benzyl bromide. The reaction is most advantageously carried out at room temperature.

Scheme 4c

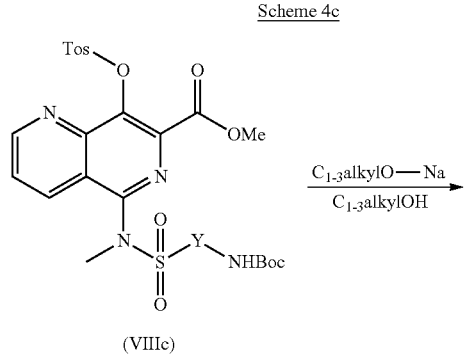

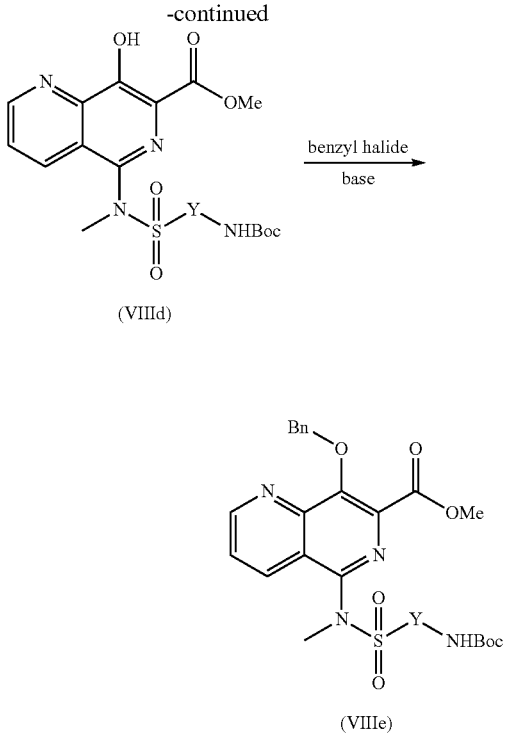

The macrocycle precursors of the general formula (IV) can be prepared in several ways, depending on the nature of the functional groups W, X and Z, as defined hereinbefore.

In a first embodiment, when W is piperazinyl, X is —C(=O)—, and Z is an oxygen atom the reaction as shown in Scheme 5a can be followed to afford the macrocycle precursor of the general formula (IVa): The piperazine of the general formula (XIII) is treated with the carboxylic acid of the general formula (XVI), in the presence of a conventional amide coupling reagent such as HBTU (O-benzotriazole-N, N,N',N'-tetramethyl uronium hexafluorophosphate), EDCI (1-ethyl-3-(3-dimethylaminopropyl)-carbodiimide), or EDAC (1-ethyl-3-(3-dimethylaminopropyl) carbodiimide hydrochloride) in an aprotic solvent like CH₂Cl₂, in the presence of an amine base additive, such as diisopropyl ethyl amine.

Scheme 5a

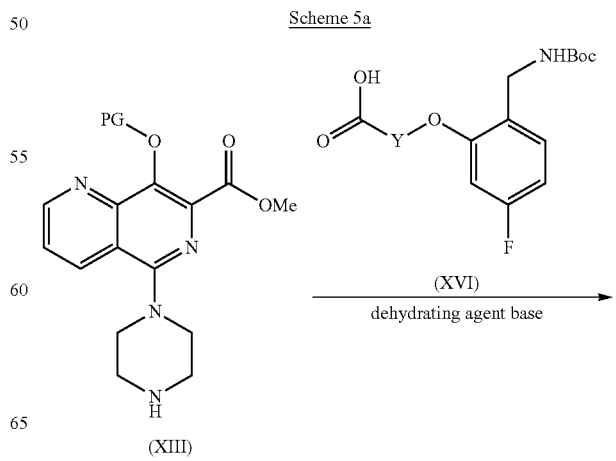

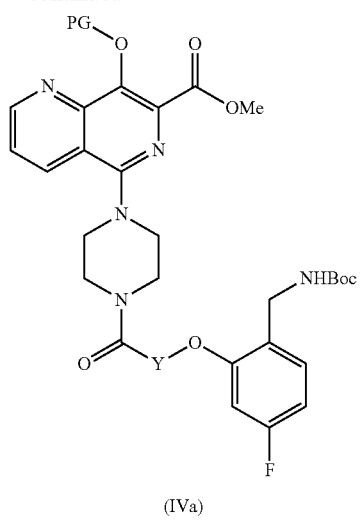

(IVa)

PG = Me or Bn

In a second embodiment, when W is —N(CH₃)—, X is —S(=O)₂—, Y is C₃₋₇alkylene, and Z is —NH—C(=O)—, the sequence as described in Scheme 5b can be followed, starting from the Boc-amino functionalized naphthyridine of the general formula (VIIIb), to afford the macrocyle precursor of the general formula (IVb). First, deprotection of the Boc-amino group in (VIIIb) can be achieved by treatment with TFA to afford the amine of the formula (XVIII). Optionally, a halogenated hydrocarbon can be used as a cosolvent, and the reaction temperature is between 0 and 20° C. Alternatively, said deprotection can be effected by using HCl in a polar, aprotic solvent, such as dioxane. In a second step, the amine of the general formula (XVIII) is treated with the carboxylic acid (XVII) in the presence of a conventional amide coupling reagent such as HBTU (O-benzotriazole-N,N,N',N'-tetramethyl uronium hexafluorophosphate), EDCI (1-ethyl-3-(3-dimethylaminopropyl)carbodiimide), or EDAC (1-ethyl-3-(3-dimethyl-aminopropyl) carbodiimide hydrochloride) in an aprotic solvent like CH₂Cl₂, or alternatively in a polar, aprotic solvent, such as DMF, or the like, in the presence of an amine base additive, such as diisopropyl ethyl amine.

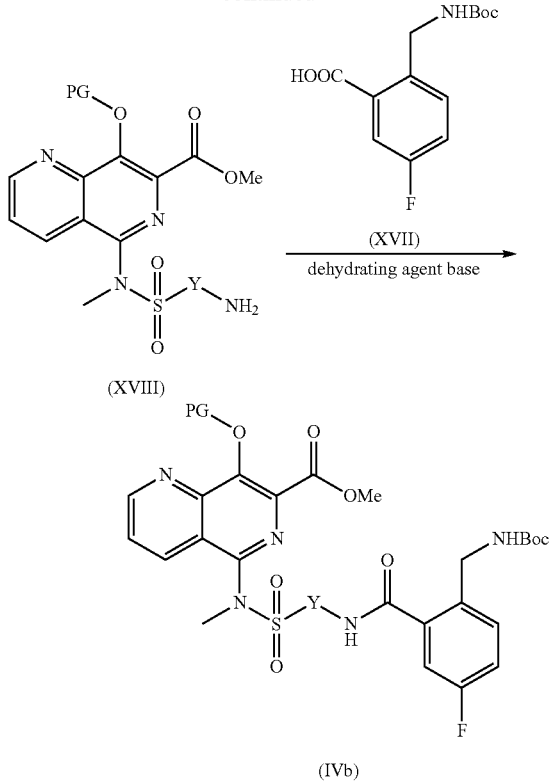

In a third embodiment, when W is —(NCH₃)—, X is —S(=O)₂—, Y is C₃₋₇alkylene, and Z is an oxygen atom, the reaction as depicted in Scheme 5c can be used, starting from the bromo naphthyridine of the general formula (XI), to afford the macrocycle precursor of the general formula (IVc). Suitable protecting groups are methyl or tosyl. The macrocycle precursor of the general formula (IVc) is prepared by reacting the bromo naphthyridine (XI) with the sulfonamide containing linker of the general formula (XIX). The use of a copper(I) base, such as copper(I) oxide, in the presence of a ligand, such as 2,2'-bipyridine offer advantages in this reaction. Useful solvents are polar, aprotic solvents, such as DMA, NMP, or the like. The reaction needs elevated temperatures, typically in the range between 80° C. and 140° C., in particular 120° C., and is generally performed in an inert atmosphere.

Scheme 5b

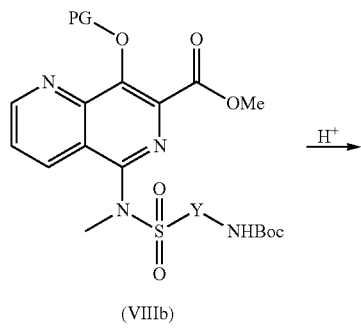

(VIIIb)

Scheme 5c

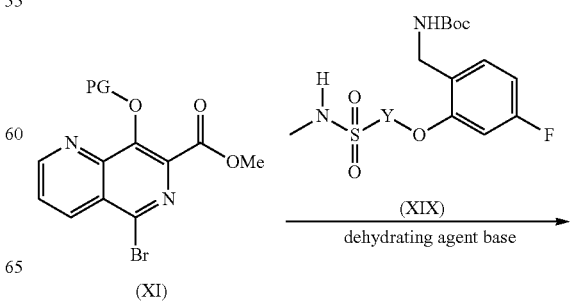

(XI)

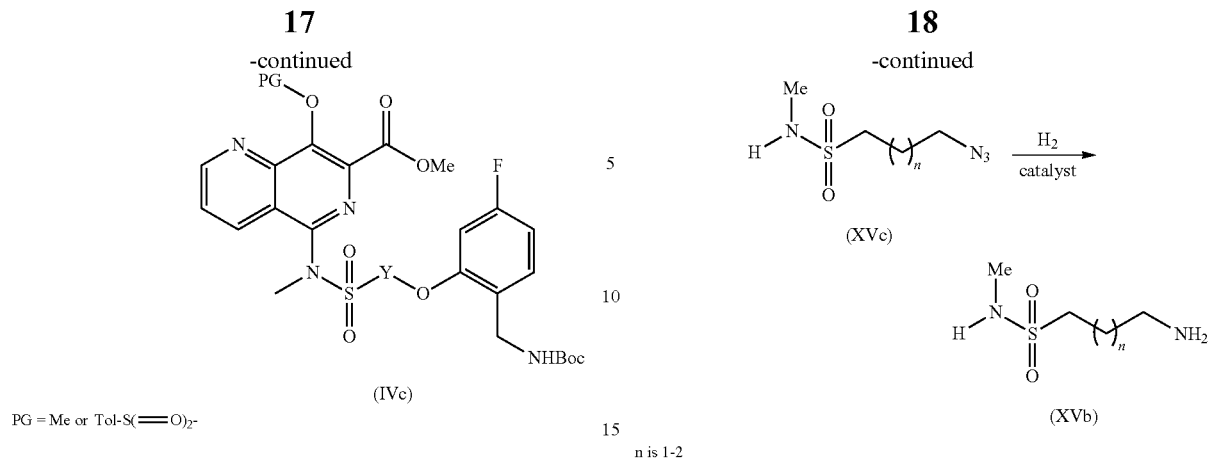

(IVc)

PG = Me or Tol-S(=O)$_2$-

To assemble the advanced intermediates and macrocyles as described in Schemes 1-5c, the building blocks as depicted in Scheme 7a-9, can be advantageously used. Said building blocks can be prepared according to the descriptions as provided hereinafter:

The Boc-amino functionalized linker of the general formula (XV) can be prepared from the amino sulfonamide of the general formula (XV'), as is depicted in Scheme 7a. Typically, a solution of the amine (XV') in a chlorinated hydrocarbon solvent, such as dichloromethane, or the like, is treated with Boc anhydride, at room temperature.

Scheme 7a

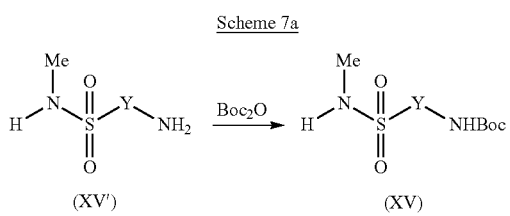

(XV')                                     (XV)

The amino functionalized linker of the general formula (XV') can be prepared from the chloro sulfonamide (XVa') in different ways, and depends on the nature of Y, as defined hereinbefore. For example, when Y is C$_{3-4}$alkyl, leading to the linker of the formula (XVb), the sequence as depicted in Scheme 7b can be followed. The chloro sulfonamide (XVa') is first treated with sodium iodide, in a polar, aprotic solvent, such as DMF, or the like, at room temperature. Next, sodium azide is added and the mixture is allowed to react in a temperature range between 20 and 70° C., in particular at 60° C., to afford the azide (XVc). In a next step, the azide is reduced to afford the amine (XVd). This transformation can be effected by putting the azide (XVc) under a hydrogen atmosphere, typically at 1 atm., in a protic solvent, such as methanol, or the like. The use of a catalyst, such as palladium on carbon, or the like, is essential to affect said hydrogenation reaction.

Scheme 7b

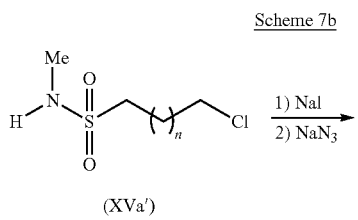

(XVa')

(XVc)

(XVb)

n is 1-2

In another example, when Y is pentylene, leading to the linker of the formula (XVd), the sequence as depicted in Scheme 7c can be followed. The chloro sulfonamide (XVa) is first treated with sodium iodide, in a polar, aprotic solvent, such as DMF, or the like, at room temperature. Next, sodium cyanide is added and the mixture is allowed to react in a temperature range between 20 and 70° C., in particular at 60° C., to afford the nitrile (XVe). In a next step, the nitrile is reduced to afford the amine (XVd). This transformation can be effected by putting the nitrile (XVe) under a hydrogen atmosphere, typically at 1 atm., in a protic solvent, such as methanol, or the like, in the presence of ammonia. The use of a catalyst, such as palladium on carbon, or the like, is essential to effect said hydrogenation reaction. Alternatively, the reduction of the nitrile function in (XVe) can be effected by treatment with borane dimethylsulfide complex at room temperature, in a polar aprotic solvent, such as THF, or the like, to afford the primary amine (XVd).

Scheme 7c

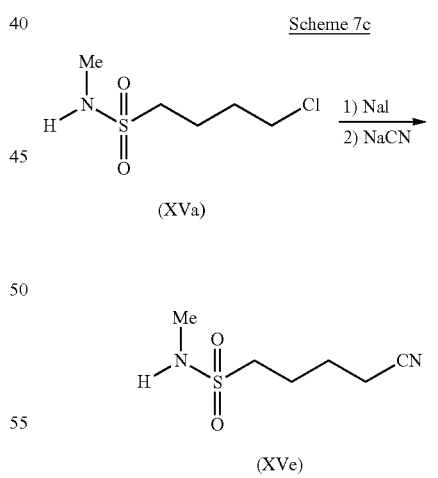

(XVa)

(XVe)

(XVd)

Scheme 7d

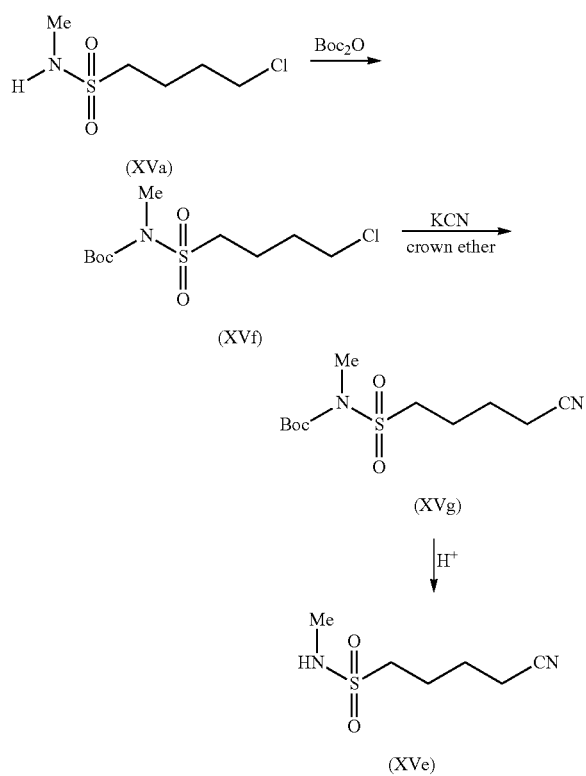

The nitrile of the formula (XVe) can also be prepared from the chloride (XVa) in three steps as is depicted in scheme 7d. The first step involves protection of the sulfonamide function with a suitable protecting group, such as Boc. This can be effected by treatment of the chloride (XVa) with Boc$_2$O at room temperature in a polar, aprotic solvent, such as DMF, or the like, to afford the Boc protected chloride (XVf). Optionally, a protic co-solvent can be used, such as methanol, or the like. The second step involves nucleophilic displacement of the chloride in (XVa) by cyanide. This can be effected by treatment of the chloride (XVa) with an inorganic cyanide salt, such as potassium cyanide, between room temperature and 150° C., in particular at 80° C., and, in a polar aprotic solvent, such as acetonitrile, or the like. It is advantageous to use a crown ether in this transformation, in particular 18-crown-6, to afford the nitrile of the formula (XVg). In a third step, deprotection of the Boc-amino group in (XVg) can be achieved by treatment with TFA to afford the cyanide of the formula (XVe). Optionally, a halogenated hydrocarbon can be used as a cosolvent, and the reaction temperature is between 0 and 20° C. Alternatively, said deprotection can be effected by using HCl in a polar, aprotic solvent, such as dioxane.

The carboxylic acid of the general formula (XVI) can be prepared in four steps from (2-(benzyloxy)-4-fluorophenyl) methanamine (XVIa), as is depicted in Scheme 8. In a first step the amine (XVIa) is protected with a Boc group. This can be effected by treatment of the amine (XVIa) in a solvent mixture consisting of dioxane and water, with Boc anhydride, in the presence of sodium carbonate, to obtain the Boc protected compound (XVIb). This reaction can be carried out in a temperature range between 0 and 20° C.

In a second step the benzyl group in (XVIb) is reductively removed by a reaction under a hydrogen atmosphere, typically at 1 atm., in a protic solvent, such as ethanol, or the like, optionally in the presence of an aprotic co-solvent, such as ethyl acetate, or the like. The use of a catalyst, such as palladium on carbon, or the like, is essential to effect said hydrogenation reaction, that affords the phenol (XVIc).

In a third step the phenol (XVIc) is reacted with a halo functionalized carboxylic ester of the general formula (XX), in the presence of an inorganic base, such as potassium carbonate, or the like. This transformation can be effected in a polar, aprotic solvent, such as DMA, or the like, in a temperature range between 20 and 80° C., in particular at 60° C., and affords the carboxylic ester of the general formula (XVId).

In a fourth step, the carboxylic ester of the general formula (XVId) is saponified to afford the carboxylic acid of the general formula (XVI). This transformation can be carried out by reaction with a metal hydroxide (M-OH), such as potassium hydroxide, or sodium hydroxide. The reaction is performed in an aqueous environment, and is most advantageously carried out in the presence of at least one water miscible organic co-solvent, such as methanol, or the like, and optionally THF.

Scheme 8

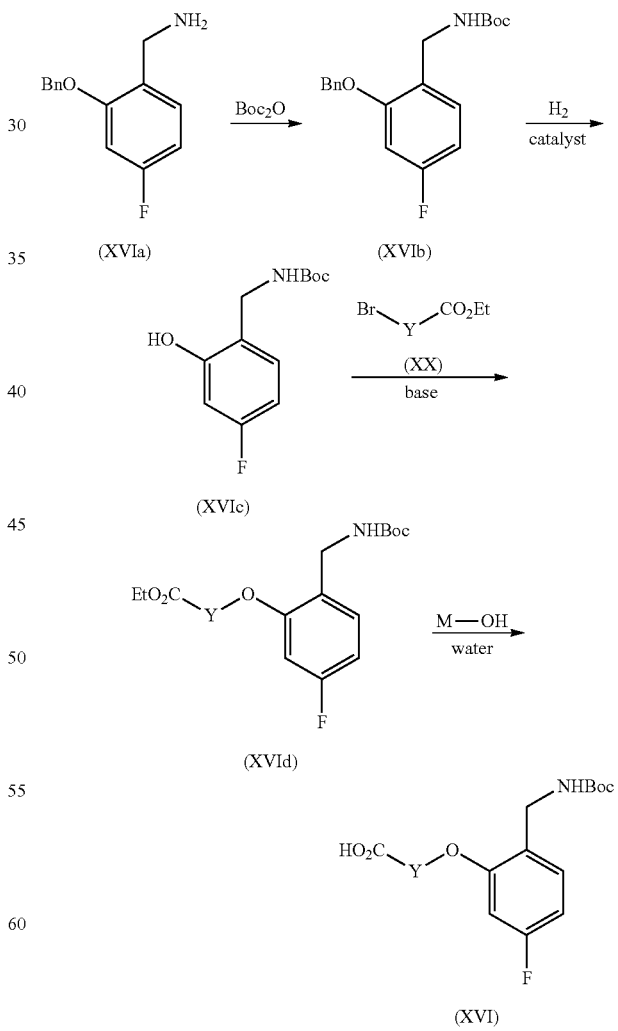

M is K, or Na

The sulfonamide building block of the general formula (XIX) can be prepared from the phenol (XVIc) and the sulfonamide of the general formula (XV''') as is shown in Scheme 9a. The sulfonamide of the general formula (XV''') contains a leaving group A, which can be halo, in particular iodo, or alternatively a tosylate. The phenol (XVIc) is reacted with (XV''') in the presence of an inorganic base, such as potassium carbonate, or the like. This transformation can be effected in a polar, aprotic solvent, such as DMF, or DMSO, or the like, in a temperature range between 20 and 80° C., in particular at 50-60° C., and affords the sulfonamide of the general formula (XIX).

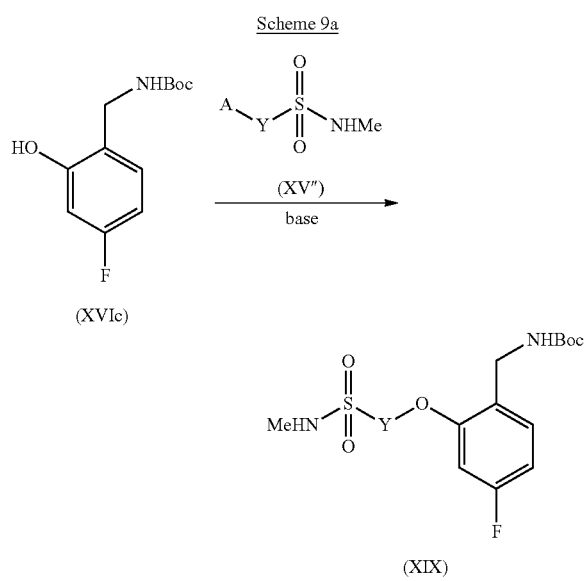

A = iodo, or tosyl-O-

The sulfonamide linker of the general formula (XV''') can be prepared using different methods, that depends on the nature of Y. For example, when Y is $C_{3-4}$alkyl, the iodo sulfonamide of the formula (XVa'') can be prepared by reaction of the corresponding chloro sulfonamide (XVa'), with sodium iodide, as is shown in Scheme 9b. This transformation is performed in acetone at reflux temperature.

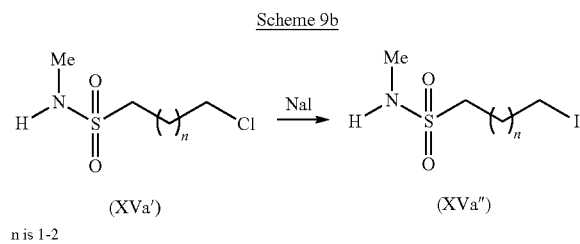

n is 1-2

In another example, when Y is $C_5$alkyl (i.e. pentylene), the tosylate (XVb'') can be prepared in three steps from the nitrile (XVe), as is shown in Scheme 9c. In a first step the nitrile (XVe) is hydrolyzed to the carboxylic acid (XVc''). This can be effected by heating in a mixture of acetic acid and hydrochloric acid, preferably at reflux temperature. In a second step the carboxylic acid function in (XVc'') is reduced to the corresponding alcohol of the formula (XVd''). This can be effected by treatment with borane in a polar aprotic solvent, such as THF or the like, at a temperature between 0 and 20° C. In a third step the hydroxyl function in (XVd'') is functionalized into a tosylate group to afford (XVb''), by reacting the alcohol (XVd'') with tosyl chloride in the presence of a tertiary amine, such as triethyl amine, or the like, in an apolar solvent, such as dichloromethane or the like, at room temperature.

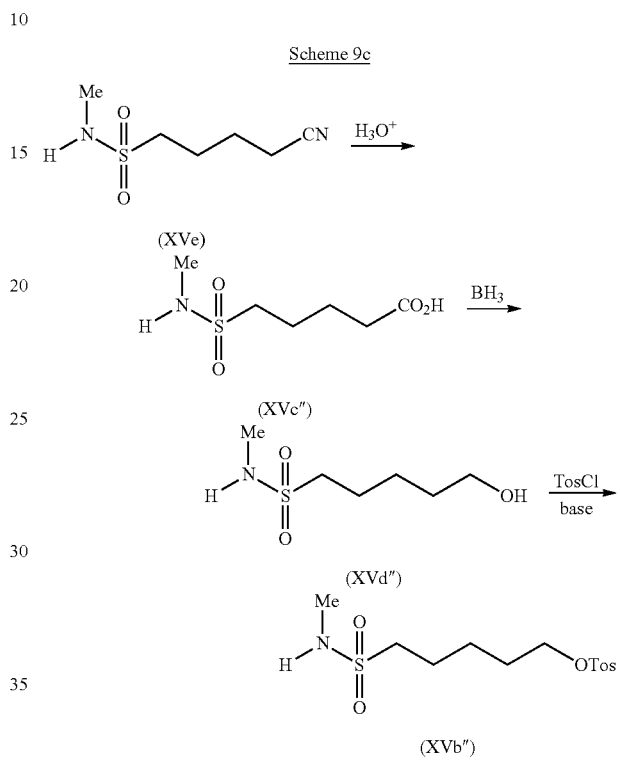

The linker precursors of the general formula (XVm) and (XVn) can be prepared as is outlined in Scheme 9d, starting from a bromo alcohol of the general formula (XVh). In a first step the alcohol in (XVh) is protected as a carboxylic ester of the general formula (XVi). Said alcohol (XVh) is treated with an acyl chloride, such as acetyl chloride or pivaloyl chloride or the like, in the presence of a tertiary amine base, such as triethyl amine, or the like, in a halogenated solvent, such as dichloro methane, or the like. The reaction can be carried out between 0° C. and room temperature. In the second step, the bromo ester of the general formula (XVi) is converted into the corresponding (amino iminomethyl)thio ether of the formula (XVj). This transformation is effected by heating a mixture of thiourea and the bromoester (XVi) in a protic solvent, such as ethanol or the like, at a temperature between 70 and 100° C. In a third step the sulfonyl chloride of the general formula (XVk) is prepared by treating the (amino iminomethyl)thio ether of the formula (XVj) with chlorine in water as the solvent at a temperature of 0° C. In a fourth step the sulfonyl chloride of the general formula (XVk) is converted into the corresponding methyl sulfonamide of the general formula (XVm) by treating a mixture of the sulfonyl chloride (XVk) with methyl amine HCl salt in a biphasic solvent system consisting of water and a halogenated hydrocarbon, such as dichloro methane, or the like. Said transformation is carried out in the presence of an inorganic base, such as potassium carbonate, or the like, at a temperature between 10 and 20° C. In a fifth step the ester protecting group in the methyl sulfonamide of the formula (XVm) is removed by treatment with a metal hydroxide, such as sodium hydroxide. The reaction is performed in an aqueous environment, and is most advantageously carried out in the presence of at least one water miscible organic co-solvent, such as methanol, ethanol or THF, or the like to afford the methyl sulfonamide alcohol of the general formula (XVn).

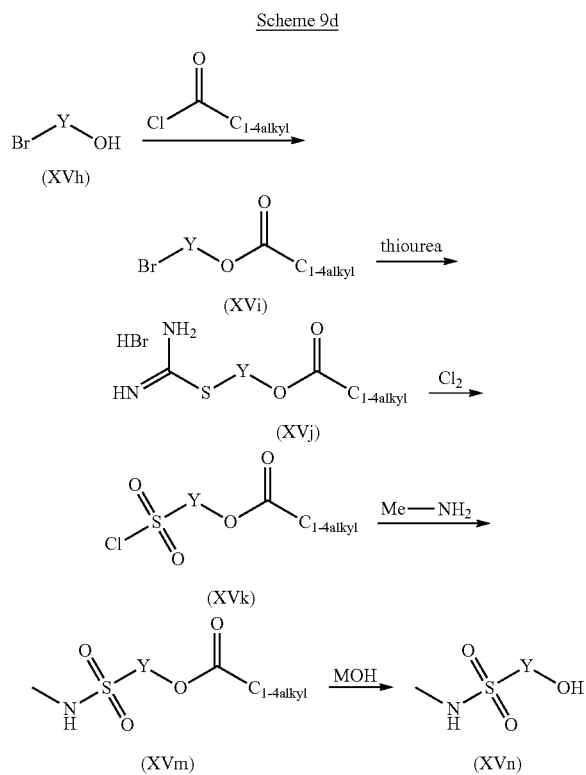

Scheme 9d

The compounds of formula (I) show antiretroviral properties (integrase inhibiting properties), in particular against HIV, the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an ever-decreasing number of T-4 cells, which moreover behave abnormally. Hence, the immunological defence system is unable to combat infections and neoplasms and the HIV infected subject usually dies by opportunistic infections such as pneumonia, or by cancers.

The compounds of the invention also show activity against drug- and multidrug-resistant HIV strains, in particular against HIV strains that have acquired resistance to one or more of the approved integrase inhibitors, in particular to raltegravir and/or elvitegravir. Major raltegravir associated resistance mutations include N155H and Q148K/R/H.

Due to their antiretroviral properties, particularly their anti-HIV properties, the compounds of formula (I) or any subgroup thereof, the pharmaceutically acceptable addition salts thereof, and the stereoisomeric forms thereof, are useful in the treatment of individuals infected by HIV and for the prophylaxis of these infections. The compounds of the present invention may also find use in the treatment of warm-blooded animals infected with viruses whose existence is mediated by, or depends upon, the enzyme protease. Conditions that may be prevented or treated with the compounds of the present invention, especially conditions associated with HIV, include AIDS, AIDS-related complex (ARC), progressive generalized lymphadenopathy (PGL), as well as chronic Central Nervous System diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the administration to HIV-infected subjects of an amount effective to combat the conditions associated with HIV and other pathogenic retroviruses, especially HIV-1. In particular, the compounds of formula (I) may be used in the manufacture of a medicament for the treatment or the prevention of HIV infections.

In a further aspect this invention provides a method of treating humans, suffering from, or a method of preventing humans to suffer from viral infections, especially HIV infections. Said method comprises the administration of an effective amount of a compound of formula (I), a pharmaceutically acceptable addition salt, a pharmaceutically acceptable solvate thereof, or a possible stereoisomeric form thereof, to humans.

The present invention also provides compositions for treating viral infections comprising a therapeutically effective amount of a compound of formula (I) and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared wherein the carrier comprises a saline solution, a glucose solution, or a mixture of saline and glucose solution. Injectable suspensions may also be prepared in which case appropriate liquid carriers, suspending agents and the like may be employed. Also included are solid form preparations that can be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines and are not intended to limit the scope or use of the invention to any extent.

Also, the combination of one or more additional antiretroviral compounds and a compound of formula (I) can be used as a medicine. Thus, the present invention also relates to a product containing (a) a compound of formula (I), and (b) one or more additional antiretroviral compounds, as a combined preparation for simultaneous, separate or sequential use in anti-HIV treatment. The different drugs may be combined in separate preparations or in a single preparation, together with pharmaceutically acceptable carriers. Said other antiretroviral compounds may be any known antiretroviral compounds such as nucleoside reverse transcriptase inhibitors (NRTIs), e.g. zidovudine (AZT), didanosine (ddI), zalcitabine (ddC), lamivudine (3TC), stavudine (d4T), emtricitabine (FTC), abacavir (ABC), amdoxovir (DAPD), elvucitabine (ACH-126,443), apricitabine (AVX 754, (−)-dOTC), fozalvudine tidoxil (FZT, HDP-990003), phosphazide, KP-1461, racivir (PSI-5004), MIV-210, and GS-9131; non-nucleoside reverse transcriptase inhibitors (NNRTIs) such as delavirdine (DLV), efavirenz (EFV), nevirapine (NVP), dapivirine (TMC120), etravirine (ETR, TMC125), rilpivirine (TMC278), IDX899, RDEA-806, UK-453601, RDEA-427, and UC-781; nucleotide reverse transcriptase inhibitors (NtRTIs), e.g. tenofovir and its pro-drug tenofovir disoproxil fumarate (TDF); protease inhibitors, e.g. ritonavir (RTV), saquinavir (SQV), lopinavir (ABT-378, LPV), indinavir (IDV), amprenavir (VX-478), nelfinavir (AG-1343), atazanavir (BMS 232,632), darunavir (TMC114), fosamprenavir (GW433908 or VX-175), brecanavir (GW-640385, VX-385), tipranavir (PNU-140690), DG-17, SPI256, PPL-100 (MK 8122), and TMC310911; entry inhibitors, which comprise fusion inhibitors (e.g. enfuvirtide (T-20) sifuvirtide, HRG-214, albuvirtide, SUC-HAS, and maC46/M87o), attachment inhibitors, modulators of intracellular cholesterol and corticosteroid biosynthesis (e.g. SP-01A), and co-receptor inhibitors, the latter comprise the CCR5 antagonists (e.g. CCR5mAb004, maraviroc (UK-427,857), PRO-140, TAK-220, TAK-652, PF232798, vicriviroc (SCH-D, SCH-417, 690), GSK-706769, nifeviroc, and SCH-532706) and CXR4 antagonists (e.g. AMD-070), further examples of entry inhibitors are TNX-355, INCB 9471, BMS-488043, nonakine, and VGV-1; maturation inhibitors, e.g. bevirimat (PA-457) and vivecon; and inhibitors of the viral integrase, e.g. raltegravir (MK-0518), elvitegravir (JTK-303, GS-9137), BMS-538158, S-349572, JTK-656 S-247303, and GS-265744.

The following examples are intended to illustrate the present invention and not to limit its scope thereto.

EXAMPLES

A. Chemical Synthesis of Compounds of Formula I

Example 1

Methyl 8-(benzyloxy)-5-bromo-1,6-naphthyridine-7-carboxylate

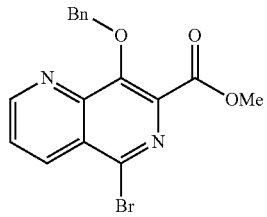 [SMILES: COC(=O)c1nc(Br)c2cccnc2c1OCc1ccccc1]

Benzyl bromide (2.53 ml, 21.2 mmol) was added to a mixture of methyl 5-bromo-8-hydroxy-1,6-naphthyridine-7-carboxylate (3.0 g; 10.6 mmol) and cesium carbonate (6.9 g; 21.2 mmol) in DMF (30 ml), under stirring at room temperature. The reaction mixture was stirred at room temperature for 12 hours. Water and ethyl acetate were added. The organic phase was separated, washed with water and with a saturated NaCl solution. The organic phase was dried, filtered and concentrated to dryness. The crude material was purified by flash chromatography column over silica gel (eluting with a gradient hexane-ethyl acetate 10:1 to 2:1).

The product fractions were collected and the solvent was evaporated.

Yield: 3.3 g (83%).

Example 2 ethyl 2-cyano-5-fluorobenzoate

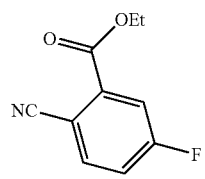 [SMILES: CCOC(=O)c1cc(F)ccc1C#N]

Zinc cyanide (26.5 g; 0.225 mol) and Pd2(dba)3 (1.9 g; 3.4 mmol) were added to a solution of ethyl 2-bromo-5-fluorobenzoate (27.9 g; 0.112 mol) in DMF (71 ml). Triphenyl phosphine (2.9 g; 11 mmol) was added and then the reaction mixture was stirred at 130° C. under nitrogen atmosphere for 4 hours. The mixture was poured out into H$_2$O (300 ml) and then extracted with EtOAc (200 ml). The organic layer was separated, washed with H$_2$O (2×100 ml), brine (100 ml), dried (MgSO$_4$), filtered and the solvent was evaporated.

The residue was purified by column chromatography over silica gel (eluent: hexanes/EtOAc (5/1, v/v)). The product fractions were collected and the solvent was evaporated.

Yield: 20 g (93%; orange solid).

Example 3

Ethyl 2-((tert-butoxycarbonylamino)methyl)-5-fluorobenzoate

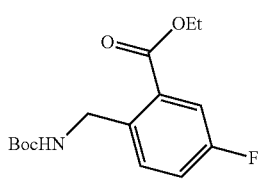 [SMILES: CCOC(=O)c1cc(F)ccc1CNC(=O)OC(C)(C)C]

A mixture of ethyl 2-cyano-5-fluorobenzoate (Example 2; 20 g; 0.10 mol), Boc$_2$O (24 ml; 0.11 mol), sodium bicarbonate (9.4 g; 0.11 mol) and Raney nickel (2 g) in THF (414 ml) was hydrogenated under a 3 bar pressure of H2 at 50° C. for 24 hours. After uptake of H2, the catalyst was removed by filtration over a Celite path and the Celite was washed with THF. The filtrate was evaporated. The residue was purified by column chromatography over silica gel (eluent: hexanes/EtOAc (5/1, v/v). The product fractions were collected and the solvent was evaporated. Yield: 15.9 g (52%)

Example 4

Ethyl 2-(aminomethyl)-5-fluorobenzoate hydrochloride

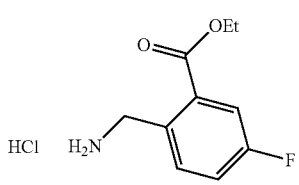 [SMILES: Cl ; CCOC(=O)c1cc(F)ccc1CN]

Concentrated HCl (37%; 16 ml) was added dropwise to a solution of thyl 2-((tert-butoxycarbonylamino)methyl)-5-fluorobenzoate (Example 3; 15.9 g; 53.6 mmol) in THF (96 ml). The mixture was heated at 50° C. for 2 hours. The mixture was concentrated to dryness. The residue was taken up in ethanol (200 ml) and concentrated again. The solid was triturated from ether (100 ml). The precipitate was filtered off and washed with diethyl ether (2×50 ml).

Yield: 8.5 g (81%; as a colourless solid).

Example 5

4-chloro-N-methylbutane-1-sulfonamide

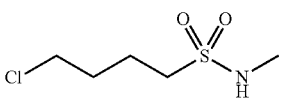

To a solution of 4-chlorobutane-1-sulfonyl chloride (117 mmol) and triethyl amine (117 mmol) in dichloro methane (250 ml) at 0° C. was added a 2M solution of methyl amine in THF (117 mmol) dropwise. The mixture was allowed to warm to room temperature with stirring overnight. The organic solution was washed with H$_2$O and extracted with CH$_2$Cl$_2$, dried over MgSO$_4$ and filtered. The solution was concentrated. The product was used without further purification.

Example 6

4-azido-N-methylbutane-1-sulfonamide

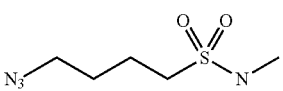

A solution of 4-chloro-N-methylbutane-1-sulfonamide (Example 5; 180 mmol), and sodium iodide (198 mmol) in DMF (180 ml) was stirred for 10 min at room temperature. Sodium azide (397 mmol) was added and the reaction mixture was stirred overnight at 60° C. The mixture was filtered off The organic phase was extracted with AcOEt/water. The crude mixture was concentrated and was used without further purification in the next step.

Example 7

4-amino-N-methylbutane-1-sulfonamide

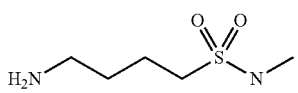

To a solution of 4-azido-N-methylbutane-1-sulfonamide (Example 6; 202 mmol), in methanol (200 ml) was added Pd/C (20 mmol Pd). The mixture put under an hydrogen atmosphere and was stirred overnight at r.t. The mixture was filtered and concentrated. The crude product was used in the next step without further purification.

Example 8 tert-butyl 4-(N-methylsulfamoyl)butylcarbamate

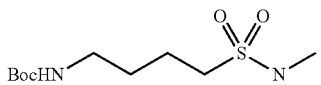 [SMILES: CNS(=O)(=O)CCCCNC(=O)OC(C)(C)C]

To a solution of 4-amino-N-methylbutane-1-sulfonamide (Example 7; 183 mmol), in dichloro methane (350 ml) was added portion wise $Boc_2O$ (183 mmol). The mixture was stirred overnight at r.t. The crude product was concentrated and purified by column chromatography ($CH_2Cl_2$:MeOH 100:1) to give the target material in 62% yield.

Example 9

4-Cyano-N-methylbutane-1-sulfonamide

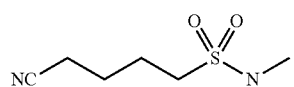

A solution of 4-chloro-N-methylbutane-1-sulfonamide (Example 5; 86.7 mmol), and sodium iodide (95.4 mmol) in DMF (175 ml) was stirred for 10 min at room temperature. Sodium cyanide (191 mmol) was added and the mixture was stirred overnight at 60° C. The mixture was filtered off and the filtrate was extracted with AcOEt/water. The crude product was concentrated and was used without further purification in the next step (Examples 10 and 20).

Example 10

5-Amino-N-methylpentane-1-sulfonamide

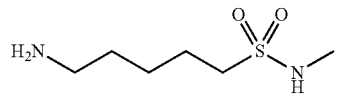

A mixture of 4-cyano-N-methylbutane-1-sulfonamide (Example 9; 91.2 mmol) and Pd/C (10 mol %, 1 g) in methanol/7N $NH_3$ (180 ml) was put under a hydrogen atmosphere. The mixture was stirred overnight at room temperature. The mixture was filtered and concentrated. The crude product was used in the next step without further purification.

Example 11 tert-Butyl 5-(N-methylsulfamoyl)pentylcarbamate

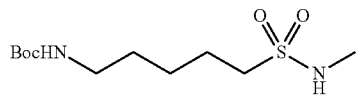 [SMILES: CNS(=O)(=O)CCCCCNC(=O)OC(C)(C)C]

To a solution of 5-Amino-N-methylpentane-1-sulfonamide (Example 10; 42.6 mmol), in dichloro methane (92 ml) was added portion wise $Boc_2O$ (42.6 mmol). The mixture was stirred overnight at room temperature. The crude product was concentrated and purified by column chromatography ($CH_2Cl_2$:MeOH 100:1) to give the target material in 50% yield.

Example 12

Methyl 5-bromo-8-(tosyloxy)-1,6-naphthyridine-7-carboxylate

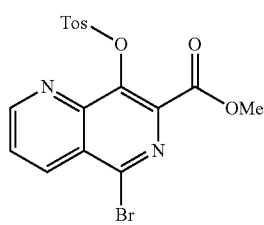

Triethyl amine (15.9 mmol) was added to a suspension of methyl 5-bromo-8-hydroxy-1,6-naphthyridine-7-carboxylate (10.6 mmol) in chloroform (22 ml) over 5 min. at 20-50° C. Tosyl chloride (12.7 mmol) was added over 5 min maintaining the temperature at 40° C. for 2 h. The mixture was cooled to 20° C. over 15 min. MeOH was added over 30 min, then a mixture of MeOH:water was added over 30 min. The resulting off-white crystalline solid was collected by filtration and dried to give the target compound in 50% yield.

Example 13

Methyl 8-(benzyloxy)-5-(piperazin-1-yl)-1,6-naphthyridine-7-carboxylate

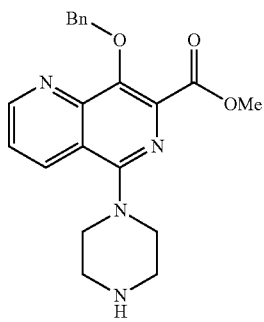 [SMILES: COC(=O)c1nc(N2CCNCC2)c2cccnc2c1OCc1ccccc1]

Diisopropyl ethyl amine (42.9 mmol) was added to a solution of methyl 8-(benzyloxy)-5-bromo-1,6-naphthyridine-7-carboxylate (Example 1; 10.7 mmol) in DMA (270 ml) at room temperature. The reaction was stirred at 5 min at. Piperazine (16.1 mmol) was added and the reaction mixture was heated at 110° C. for 12 hr.

The reaction was cooled, water and ethyl acetate was added. The organic layer was separated and washed with water (×2) and with brine. The organic layer was dried (MgSO$_4$), filtered and evaporated.

The residue was purified by flash-chromatography on SiO2 with (Hex/AcOEt 10:1-1:1), to give the title compound (1.5 g) as a pale yellow solid.

Example 14

Tert-butyl 2-(benzyloxy)-4-fluorobenzylcarbamate

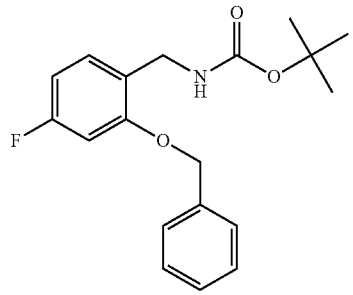 [SMILES: CC(C)(C)OC(=O)NCc1ccc(F)cc1OCc1ccccc1]

(2-(Benzyloxy)-4-fluorophenyl)methanamine was dissolved in 1,4-dioxane (22 ml). Water (6 ml) and 1M Na$_2$CO$_3$ solution (55 ml) were added. The reaction mixture was cooled to 0° C. Boc$_2$O was added dropwise. The ensuing mixture was allowed to warm to r.t. and stirred at r.t. for 24 hours.

The reaction mixture was filtered and washed with CH$_2$Cl$_2$ and water (×2). The phases were separated and the organic layer was dried with MgSO$_4$, filtered and concentrated to afford the crude target compound as a yellow solid (5.75 g). This material was combined with batches from separate experiments, and further purified by column chromatography over SiO$_2$ (Hexanes/AcOEt, 8/1, v/v) to afford the target compound (97% purity) as a colorless solid.

Example 15

Tert-butyl 4-fluoro-2-hydroxybenzylcarbamate

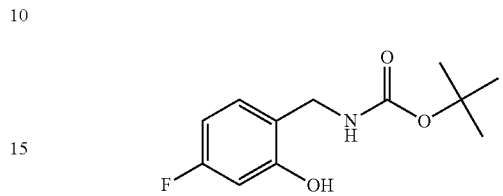

A solution of tert-butyl 2-(benzyloxy)-4-fluorobenzylcarbamate (Example 14; 9 mmol) in EtOH (80 ml) and ethyl acetate (240 ml) was treated with 1 atm of hydrogen at 25° C. over 10% Pd/C (0.4 gr) for 24 hours. The catalyst was removed by filtration through celite, washed with EtOH and the filtrate was concentrated to afford the title compound (2.2 g) as a yellow solid.

Example 16

Ethyl 5-(2-((tert-butoxycarbonylamino)methyl)-5-fluorophenoxy)-pentanoate

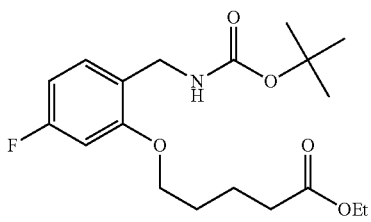 [SMILES: CCOC(=O)CCCCOc1cc(F)ccc1CNC(=O)OC(C)(C)C]

Ethyl 5-bromopentanoate (14.9 mmol) was added dropwise over 15 minutes to a mixture of tert-butyl 4-fluoro-2-hydroxybenzylcarbamate (Example 15; 12.4 mmol) and potassium carbonate (16.1 mmol) in DMA (37 ml). The reaction was heated at 60° C. for 4 hours, followed by the addition of another amount of ethyl 5-bromopentanoate (4.5 mmol) and potassium carbonate (4.8 mmol) and heating at 60° C. for 2 hours. The solvent was evaporated. The residue was taken up in AcOEt and filtered. The filtrate was washed with AcOEt (×3) and concentrated in vacuo. The residue was purified by

Example 17

5-(2-((Tert-butoxycarbonylamino)methyl)-5-fluorophenoxy)pentanoic acid

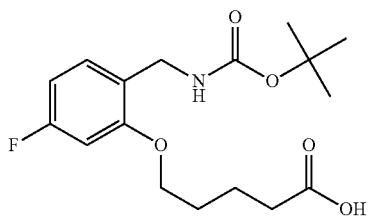 [SMILES: CC(C)(C)OC(=O)NCc1ccc(F)cc1OCCCCC(=O)O]

Ethyl 5-(2-((tert-butoxycarbonylamino)methyl)-5-fluorophenoxy)pentanoate (Example 16; 1.6 mmol) was dissolved in a mixture of THF (6 ml), methanol (6 ml) and water (6 ml). Sodium hydroxide (5.0 mmol) was added and stirred for 2 h. The organic solvent was removed under vacuum, and the aqueous residue was acidified with 1 N HCl to pH=3. The mixture was extracted with ethyl acetate, and the organic phase was removed under vacuum to afford the title compound (0.55 gr) that was used as such in the next step (Example 5.1).

Example 18

4-Iodo-N-methylbutane-1-sulfonamide

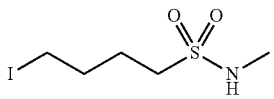

in acetone (600 ml) was stirred at refluxed overnight. The mixture was allowed to cool to room temperature and filtered. The filtrate was concentrated in vacuo to afford the title compound (40 g), that was used as such in the next step (Example 19).

Example 19

Tert-butyl 4-fluoro-2-(4-(N-methylsulfamoyl)butoxy)benzylcarbamate

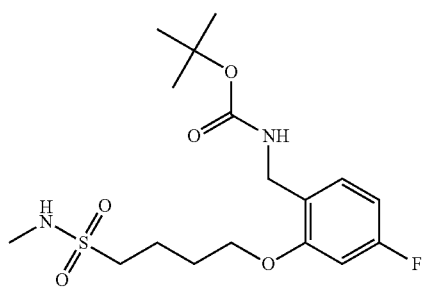 [SMILES: CNS(=O)(=O)CCCCOc1cc(F)ccc1CNC(=O)OC(C)(C)C]

A mixture of tert-butyl 4-fluoro-2-hydroxybenzylcarbamate (Example 15; 12.2 mmol), 4-iodo-N-methylbutane-1-sulfonamide (Example 18; 18.3 mmol) and potassium carbonate (61 mmol) in DMF (60 ml) was stirred at 80° C. for 10 hours.

The reaction mixture was filtered off and the residue was washed with ethyl acetate.

The filtrate was concentrated and water was added.

The mixture was extracted with ether and the organic layer was separated, dried over $MgSO_4$, filtered off and concentrated to give the crude product. The crude product was combined with another batch from a separate experiment and then purified by RP preparative high-performance liquid chromatography (eluent: $MeOH/H_2O$ from 50/50 to 80/20, 0.1% CF3COOH).

The pure fractions were collected and saturated $NaHCO_3$ solution was added.

The solvent was concentrated under vacuum and then extracted with dichloromethane.

The organic layer was dried over $MgSO_4$, filtered off and concentrated to give the target compound (1.1 gr, 13% yield).

Example 20

5-(N-Methylsulfamoyl)pentanoic acid

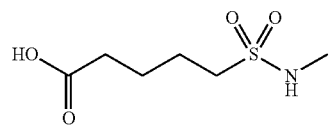

A mixture of 4-cyano-N-methylbutane-1-sulfonamide (Example 9; 100 mmol), acetic acid (100 ml) and concentrated hydrochloric acid (100 ml) was refluxed for 5 hours and then concentrated in vacuo. The residue was taken on THF and then filtered off. The filtrate was concentrated and the residue was washed with dichloromethane to give the pure product (11 g; 58% yield).

Example 21

5-Hydroxy-N-methylpentane-1-sulfonamide

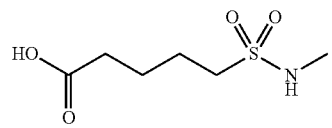

To a cooled solution of 5-(N-methylsulfamoyl)pentanoic acid (Example 20; 26 mmol) in THF (50 ml) was added a solution of borane in THF (77 mmol) at 0° C.

The reaction mixture was allowed to warm to room temperature and refluxed for 3 hours. Methanol was added and the mixture was concentrated in vacuo to give the crude product. The crude product was purified by flash column

Example 22

5-(N-Methylsulfamoyl)pentyl 4-methylbenzenesulfonate

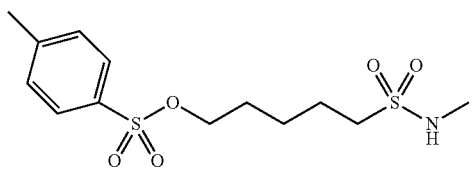

To a solution of 5-hydroxy-N-methylpentane-1-sulfonamide (Example 21; 6.4 mmol) and triethyl amine (19.2 mmol) in THF (15 ml) was added para toluenesulfonyl chloride (5.9 mmol) in THF (5 ml) at room temperature and the reaction mixture was stirred for 10 hours. The reaction mixture was washed by saturated $NaHCO_3$ solution and then brine. The organic layer was dried over $MgSO_4$, filtered off and concentrated. The residue was purified by flash column chromatography ($SiO_2$; eluent: petroleum ether/ethyl acetate from 100/0 to 50/50) to give the pure title compound (0.9 gr; 41% yield.

Example 23

Tert-butyl 4-fluoro-2-(5-(N-methylsulfamoyl)pentyloxy)benzylcarbamate

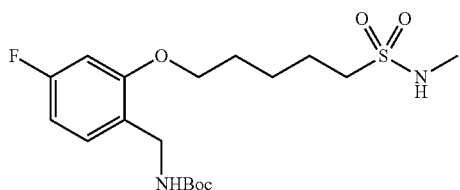 [SMILES: CNS(=O)(=O)CCCCCOc1cc(F)ccc1CNC(=O)OC(C)(C)C]

A mixture of 5-(N-methylsulfamoyl)pentyl 4-methylbenzenesulfonate (Example 22; 2.6 mmol), tert-butyl 4-fluoro-2-hydroxybenzylcarbamate (Example 15; 2.1 mmol) and potassium carbonate (6.3 mmol) in DMSO (20 ml) was stirred at 50° C. under nitrogen atmosphere for 2 hours. The reaction mixture was taken on in dichloromethane and filtered off. The filtrate was washed with saturated $NaHCO_3$ solution and brine. The organic layer was concentrated in vacuo and then methyl t-butyl ether was added. The mixture was washed with brine and the organic layer was dried over $MgSO_4$, filtered off and concentrated in vacuo to give the crude product.

The crude product was purified by flash column chromatography ($SiO_2$; eluent: petroleum ether/ethyl acetate from 100/0 to 50/50) to give the pure title compound (0.7 gr; 82% yield).

Example 1.1

Methyl 8-(benzyloxy)-5-(6-(tert-butoxycarbonylamino)hexylamino)-1,6-naphthyridine-7-carboxylate

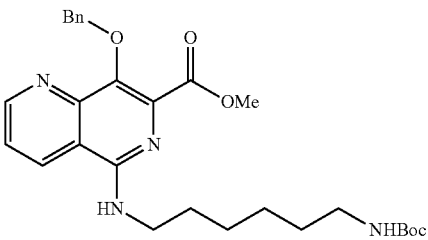 [SMILES: COC(=O)c1nc(NCCCCCCNC(=O)OC(C)(C)C)c2cccnc2c1OCc1ccccc1]

Methyl 8-(benzyloxy)-5-bromo-1,6-naphthyridine-7-carboxylate (Example 1; 5.50 g; 14.7 mmol) was dissolved in DMA (300 ml). DIPEA (5.14 ml; 29.5 mmol) was added at room temperature. The reaction mixture was stirred for 5 min at room temperature. tert-Butyl 6-aminohexylcarbamate (4.95 ml; 22.1 mmol) was added and the reaction mixture was stirred at 100° C. for 12 hours. The reaction mixture was cooled. Water and ethyl acetate were added. The organic layer was separated and washed with water (×2) and with brine. The organic layer was dried ($MgSO_4$), filtered and the solvent was evaporated. The residue was purified by flash column chromatography over silica gel (eluent: hexane/EtOAc from 10:1 to 1:1). The product fractions were collected and the solvent evaporated.

Yield: 33%; pale yellow solid

Example 1.2

8-(Benzyloxy)-5-(6-(tert-butoxycarbonylamino)hexylamino)-1,6-naphthyridine-7-carboxylic acid

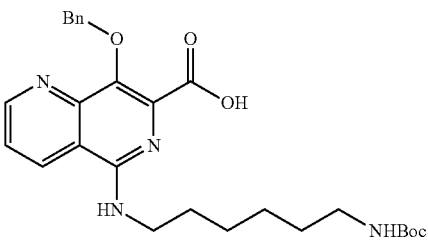 [SMILES: CC(C)(C)OC(=O)NCCCCCCNc1nc(C(=O)O)c(OCc2ccccc2)c2ncccc12]

Methyl 8-(benzyloxy)-5-(6-(tert-butoxycarbonylamino)hexylamino)-1,6-naphthyridine-7-carboxylate (Example 1.1; 0.58 g; 1.08 mmol) was dissolved in a mixture of water (2 ml) and methanol (2 ml). NaOH (100 mg; 2.7 mmol) was added at room temperature. The reaction mixture was stirred at room temperature for 4 hours. $H_2O$ and HCl 2 N were added until pH=4-5 was reached. The mixture was extracted with EtOAc (2×). The organic layer was separated, dried ($MgSO_4$), filtered and the solvent was evaporated.

Yield: 563 mg (95%).

Example 1.3

Ethyl 2-((8-(benzyloxy)-5-(6-(tert-butoxycarbonylamino)hexylamino)-1,6-naphthyridine-7-carboxamido)methyl)-5-fluorobenzoate

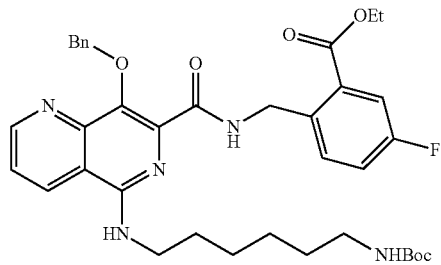

8-(Benzyloxy)-5-(6-(tert-butoxycarbonylamino)hexylamino)-1,6-naphthyridine-7-carboxylic acid (Example 1.2; 0.42 g; 0.85 mmol) was dissolved in dichloro methane (9 ml). DIPEA (0.58 ml; 3.42 mmol) and HBTU (0.39 g; 1.03 mmol) were added. The reaction mixture was stirred at room temperature during 5 min. Ethyl 2-(aminomethyl)-5-fluorobenzoate hydrochloride (Example 4; 0.24 g; 1.03 mmol) was added portionwise at room temperature. The mixture was stirred overnight at room temperature. The mixture was diluted with $CH_2Cl_2$ and washed with a saturated aqueous $Na_2CO_3$ solution (2x) and $H_2O$. The organic layer was separated, dried ($MgSO_4$), filtered and evaporated. The residue was purified by flash column chromategraphy over silica gel (eluent: hexane/EtOAc 10:1 up to 1:1). The fractions were collected and the solvent evaporated.

Yield: 0.643 g

Example 1.4

2-((8-(Benzyloxy)-5-(6-(tert-butoxycarbonylamino)hexylamino)-1,6-naphthyridine-7-carboxamido)methyl)-5-fluorobenzoic acid

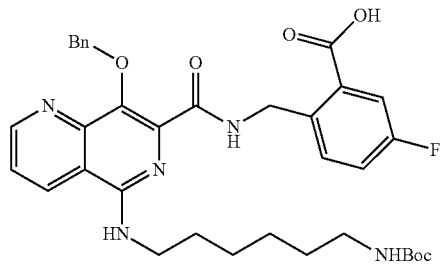 [SMILES: CC(C)(C)OC(=O)NCCCCCCNc1nc(C(=O)NCc2ccc(F)cc2C(=O)O)c(OCc2ccccc2)c2ncccc12]

Ethyl 2-((8-(benzyloxy)-5-(6-(tert-butoxycarbonylamino)hexylamino)-1,6-naphthyridine-7-carboxamido)methyl)-5-fluorobenzoate (Example 1.3; 0.64 g; 0.96 mmol) was dissolved in ethanol (4 ml). A solution of 1N NaOH (1.5 ml) was added at room temperature. After completion of the reaction, HCl 1 N was added until pH=2-3 was reached. The solvent was evaporated under pressure. The residue was taken-up in EtOAc and washed with $H_2O$ and brine. The organic layer was separated, dried ($MgSO_4$), filtered and the solvent was evaporated under reduced pressure. Yield: 0.592 g (96%; used in next reaction step, without further purification).

Example 1.5

2-((5-(6-Aminohexylamino)-8-(benzyloxy)-1,6-naphthyridine-7-carboxamido)methyl)-5-fluorobenzoic acid, TFA salt

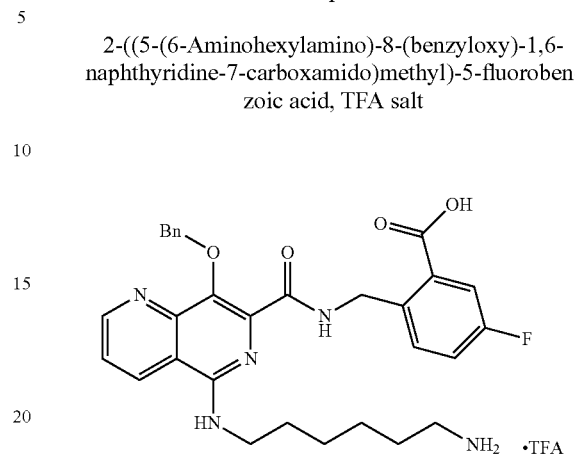

A solution of $CH_2Cl_2$ (3.6 ml), trifluoro acetic acid (3.6 ml) and triisopropyl silane (0.075 ml) was prepared.

2-((8-(Benzyloxy)-5-(6-(tert-butoxycarbonylamino)hexylamino)-1,6-naphthyridine-7-carboxamido)methyl)-5-fluorobenzoic acid (Example 1.4; 0.48 g; 0.74 mmol) was dissolved in dichloromethane (4 ml), and cooled to 0° C. The above prepared solution was added to this cold solution, and the reaction mixture was stirred and gradually warmed from 0° C. up to room temperature during 1 hour. The solvent was evaporated under reduced pressure and the residue was distilled azeotropically with toluene (2x). The resulting residue was dried under high-vacuum and used in the next step without further purification.

Yield: 0.420 g (96%).

Example 1.6

Macrocyclization

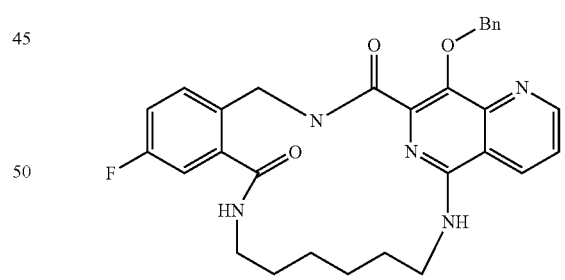

A solution of 2-((5-(6-aminohexylamino)-8-(benzyloxy)-1,6-naphthyridine-7-carboxamido)methyl)-5-fluorobenzoic acid, TFA salt (Example 1.5; 0.42 g; 0.74 mmol) in DMF (40 ml) was slowly added to a solution of HBTU (0.84 g; 2.22 mmol) and DIPEA (3.77 ml; 22.2 mmol) in DMF (150 ml) at room temperature over 4 hours. The reaction mixture was concentrated. NH4OH (3 ml) was added, and the mixture was stirred for 30 min at room temperature. The solvent was evaporated till dryness. The residue was partitioned between dichloromethane and a saturated aqueous of $NaHCO_3$ solution (x2). The layers were separated. The organic layer was dried ($MgSO_4$), filtered and the solvent was evaporated. The crude material was purified by flash column chromatography over silica gel (eluent: $CH_2Cl_2$/MeOH from 80:1 up to 20:1). The product fractions were collected and the solvent was evaporated. The residue was triturated from acetonitrile, the product was collected by filtration and dried.

Yield: 0.080 g (colorless crystals).

Example 2.1

Methyl 5-(5-(tert-butoxycarbonylamno)-N-methyl-pentylsulfonamido)-8-(tosyloxy)-1,6-naphthyridine-7-carboxylate

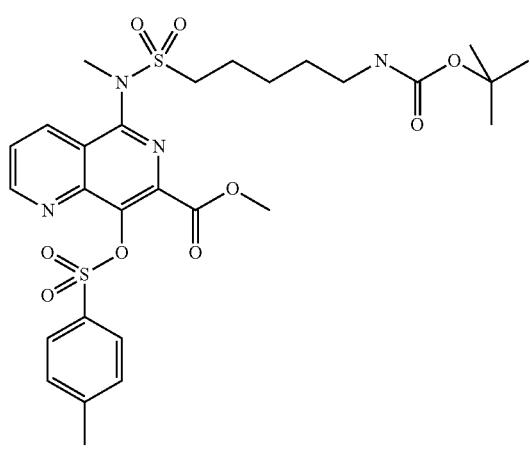 [SMILES: COC(=O)c1nc(N(C)S(=O)(=O)CCCCCNC(=O)OC(C)(C)C)c2cccnc2c1OS(=O)(=O)c1ccc(C)cc1]

A mixture of methyl 5-bromo-8-(tosyloxy)-1,6-naphthyridine-7-carboxylate (Example 12; 10.3 mmol), tert-Butyl 5-(N-methylsulfamoyl)pentylcarbamate (Example 11; 12.4 mmol), 2,2'-bipyridine (12.4 mmol) and copper (I) oxide (12.4 mmol) in DMF (22 ml) was degassed by stirring under a stream of nitrogen for 1 min and heated to 120° C. for 4 h. The brown suspension became a dark red solution with a small amount of undissolved copper (I) oxide. The mixture was diluted with chloroform, celite was added and the resulting mixture was filtered through a plug of celite. The plug was washed with chloroform and the combined filtrates were stirred vigorously with a solution of EDTA in water while nitrogen was slowly bubbled in for 30 min. The upper aqueous phase become green while the lower organic phase became yellow. The organic phase was washed with a solution of EDTA in water. The organic phases were dried over $MgSO_4$ and concentrated. The residue was purified by $SiO_2$ column chromatography (5:1 to 1:1, hexanes:ethyl acetate) to give the target product in 70% yield.

Example 2.2

Methyl 5-(5-(tert-butoxycarbonylamino)-N-methyl-pentylsulfonamido)-8-hydroxy-1,6-naphthyridine-7-carboxylate

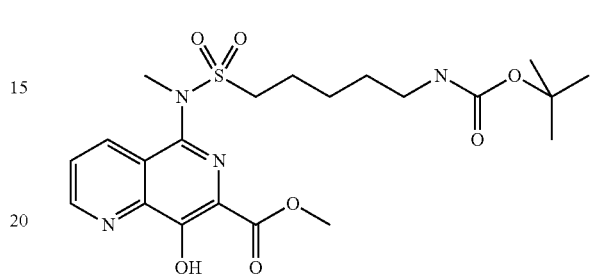

Methyl 5-(5-(tert-butoxycarbonylamino)-N-methylpen-tylsulfonamido)-8-(tosyloxy)-1,6-naphthyridine-7-carboxylate (Example 2.1; 8.68 mmol) was dissolved in DMF (17 ml) at 40° C. and transferred to a 33% solution of NaOMe in MeOH (4.1 ml; 21.7 mmol) over 1-2 min at 25° C. The resulting yellow homogenous mixture was heated to 50° C. Mixture was cooled to 25° C. over 15 min and aged at 25° C. for 15 min. Acetic acid (1 ml) was added over 1 min, then water was added. The slurry was aged for 30 min and filtered. The filter cake was washed with water, and dried to give the target compound in 61% yield.

Example 2.3

Methyl 8-(benzyloxy)-5-(5-(tert-butoxycarbony-lamino)-N-methylpentyl-sulfonamido)-1,6-naphthyridine-7-carboxylate

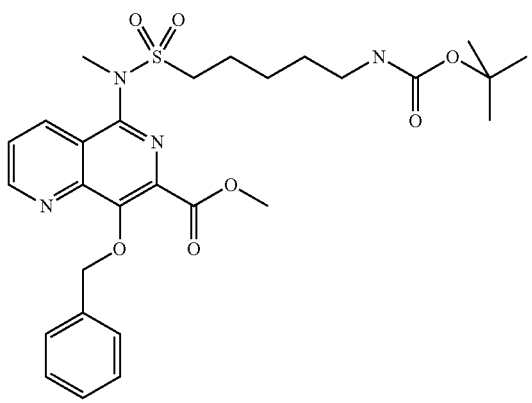 [SMILES: COC(=O)c1nc(N(C)S(=O)(=O)CCCCCNC(=O)OC(C)(C)C)c2cccnc2c1OCc1ccccc1]

To a suspension of methyl 5-(5-(tert-butoxycarbony-lamino)-N-methylpentylsulfonamido)-8-hydroxy-1,6-naphthyridine-7-carboxylate (Example 2.2; 5.44 mmol), and $Cs_2CO_3$ (10.9 mmol) in DMF (11 ml) was added benzyl bromide (10.9 mmol). The mixture was stirred overnight. The crude mixture was extracted with AcOEt/water, dried over MgSO₄ and concentrated. The product was purified by SiO₂ column chromatography (1:1, AcOEt:Hex), to give the target compound in 75% yield.

Example 2.4

8-(benzyloxy)-5-(5-(tert-butoxycarbonylamino)-N-methylpentylsulfonamido)-1,6-naphthyridine-7-carboxylic acid

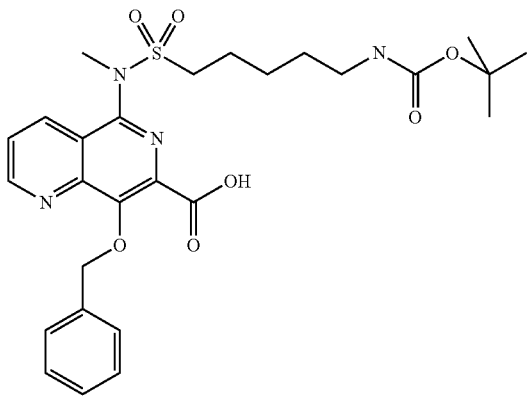 [SMILES: CN(c1nc(C(=O)O)c(OCc2ccccc2)c2ncccc12)S(=O)(=O)CCCCCNC(=O)OC(C)(C)C]

To a solution of methyl 8-(benzyloxy)-5-(5-(tert-butoxycarbonylamino)-N-methylpentylsulfonamido)-1,6-naphthyridine-7-carboxylate (Example 2.3; 4.05 mmol) in methanol (8 ml) and water (8 ml) at rt was added sodium hydroxide (16.2 mmol). The reaction was heated at 50° C. Ethyl acetate was added and the aquous phase was treated with HCl 1N until pH=6-7. Ethyl acetate was added again, the layers were separated and the organic phase was dried with MgSO₄ and concentrated. The crude product was obtained in 94% yield, and used in the next step without further purification.

Example 2.5

Ethyl 2-((8-(benzyloxy)-5-(5-(tert-butoxycarbonylamino)-N-methylpentylsulfonamido)-1,6-naphthyridine-7-carboxamido)methyl)-5-fluorobenzoate

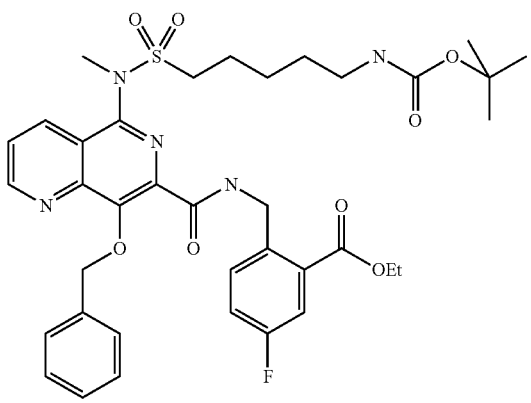 [SMILES: CCOC(=O)c1cc(F)ccc1CNC(=O)c1nc(N(C)S(=O)(=O)CCCCCNC(=O)OC(C)(C)C)c2cccnc2c1OCc1ccccc1]

To a solution of 8-(benzyloxy)-5-(5-(tert-butoxycarbonylamino)-N-methylpentylsulfonamido)-1,6-naphthyridine-7-carboxylic acid (Example 2.4; 3.82 mmol) in dichloro methane (38 ml) were added HBTU (4.58 mmol) and DIPEA (15.8 mmol). The mixture was stirred for 5 min at rt. Ethyl 2-(aminomethyl)-5-fluorobenzoate hydrochloride (Example 4; 4.58 mmol) was added portionwise at rt. The mixture was stirred overnight at rt. The product was extracted with CH₂Cl₂, dried over MgSO₄ and concentrated. The crude product was purified by SiO₂ column chromatography (AcOEt:Hex, 1:1) to afford the target compound in 71% yield.

Example 2.6

2-((5-(5-amino-N-methylpentylsulfonamido)-8-hydroxy-1,6-naphthyridine-7-carboxamido)methyl)-5-fluorobenzoic acid, HCl salt

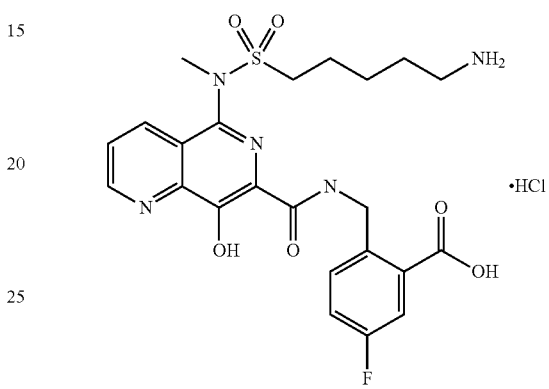

To a solution of ethyl 2-((8-(benzyloxy)-5-(5-(tert-butoxycarbonylamino)-N-methylpentylsulfonamido)-1,6-naphthyridine-7-carboxamido)methyl)-5-fluorobenzoate (Example 2.5; 2.71 mmol) in ethanol was added concentrated HCl (37%; 1.1 ml) at rt. The reaction mixture was heated at 100° C. for 3 days. The solvent was evaporated and the crude product was used in the next step without further purification.

Example 3.1

Methyl 5-(4-(tert-butoxycarbonylamino)-N-methylbutylsulfonamido)-8-(tosyloxy)-1,6-naphthyridine-7-carboxylate

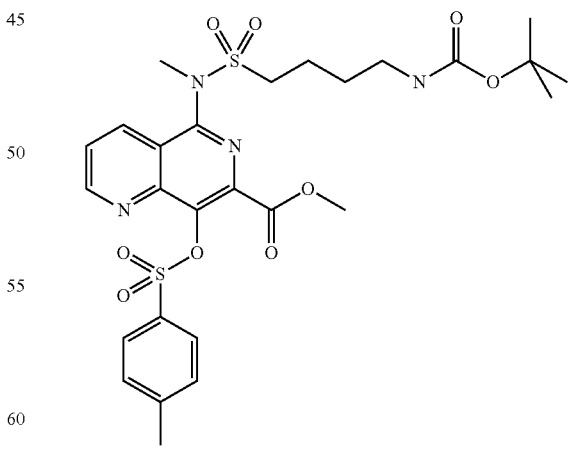

The title compound was prepared in a similar fashion as described in Example 2.1, starting from methyl 5-bromo-8-(tosyloxy)-1,6-naphthyridine-7-carboxylate (Example 12; 10.3 mmol) and tert-butyl 4-(N-methylsulfamoyl)butylcarbamate (Example 8) to obtain the target compound (3.43 gr).

Example 3.2

Methyl 5-(4-amino-N-methylbutylsulfonamido)-8-(tosyloxy)-1,6-naphthyridine-7-carboxylate

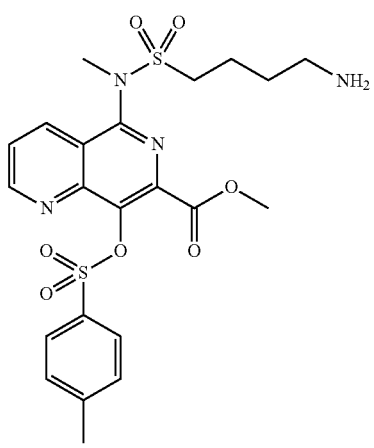 [SMILES: COC(=O)c1nc(N(C)S(=O)(=O)CCCCN)c2cccnc2c1OS(=O)(=O)c1ccc(C)cc1]

To a solution of methyl 5-(4-(tert-butoxycarbonylamino)-N-methylbutylsulfonamido)-8-(tosyloxy)-1,6-naphthyridine-7-carboxylate (Example 3.1; 5.52 mmol) in dichloro methane (5 mL) was added trifluoro acetic acid (5 mL) at 0° C. After addition the reaction was warmed to room temperature. The solvent was evaporated and the residue was co-evaporated with toluene (3×). The resulting residue was dried under vacuum and used in the next step (Example 3.3) without further purification.

Example 3.3

Methyl 5-(4-(2-((tert-butoxycarbonylamino)methyl)-5-fluorobenzamido)-N-methylbutylsulfonamido)-8-(tosyloxy)-1,6-naphthyridine-7-carboxylate

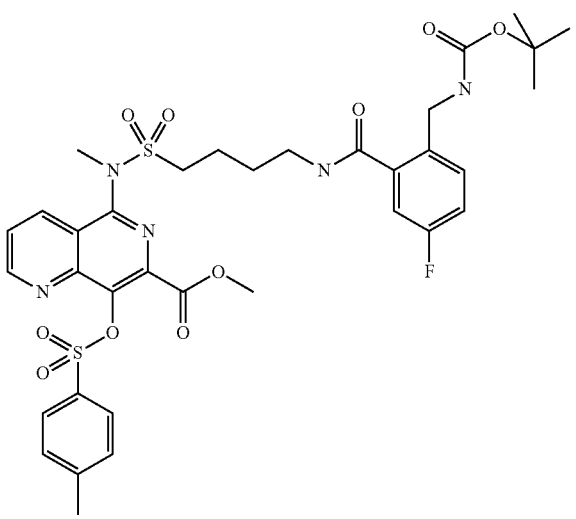 [SMILES: COC(=O)c1nc(N(C)S(=O)(=O)CCCCNC(=O)c2cc(F)ccc2CNC(=O)OC(C)(C)C)c2cccnc2c1OS(=O)(=O)c1ccc(C)cc1]

To a solution of methyl 5-(4-amino-N-methylbutylsulfonamido)-8-(tosyloxy)-1,6-naphthyridine-7-carboxylate (Example 3.2; 5.52 mmol) in dichloro methane (5 mL) was added DIPEA (18.7 mmol) and HBTU (5.63 mmol). The mixture was stirred for 5 min at rt. 2((Tert-butoxycarbonylamino)methyl)-5-fluorobenzoic acid (4.69 mmol) was added portionwise at room temperature. The mixture was stirred overnight at room temperature. The solvent was evaporated. The residue was washed with a 1M $Na_2CO_3$ solution. The aqueous phase was extracted with dichloro methane, dried and was concentrated. The crude product was purified by $SiO_2$ column chromatography (5:1 to 1:1 hexanes:ethyl acetate) to give the target compound in 49% yield.

Example 3.4

5-(4-(2-((Tert-butoxycarbonylamino)methyl)-5-fluorobenzamido)-N-methylbutylsulfonamido)-8-(tosyloxy)-1,6-naphthyridine-7-carboxylic acid

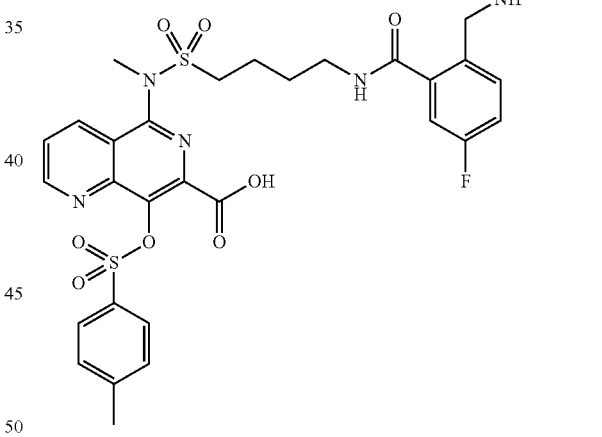

To a solution of methyl 5-(4-(2-((tert-butoxycarbonylamino)methyl)-5-fluorobenzamido)-N-methylbutylsulfonamido)-8-(tosyloxy)-1,6-naphthyridine-7-carboxylate (Example 3.3; 2.75 mmol) in a 1:1 mixture of THF and water (5.5 mL) was added lithium hydroxide (4.13 mmol) at room temperature. After the reaction was finished, ethyl acetate and water were added. The aquous layer was treated with HCl 1N until pH=5-6. The aqueous layer was extracted with ethyl acetate. The organic layer was dried over MgSO$_4$ and concentrated, to obtain the target material in 41% yield.

Example 3.5

5-(4-(2-(Aminomethyl)-5-fluorobenzamido)-N-methylbutylsulfonamido)-8-(tosyloxy)-1,6-naphthyridine-7-carboxylic acid, TFA salt

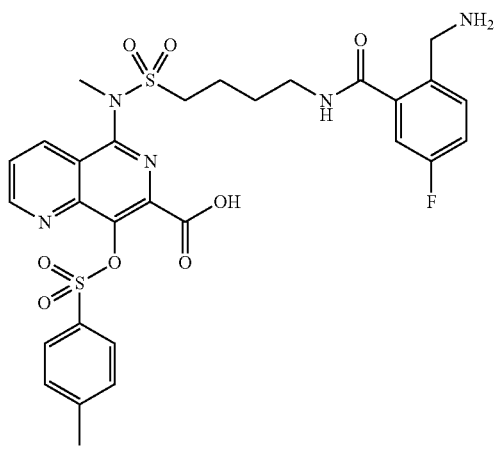 [SMILES: Cc1ccc(S(=O)(=O)Oc2c(C(=O)O)nc(N(C)S(=O)(=O)CCCCNC(=O)c3cc(F)ccc3CN)c3cccnc23)cc1]

The title compound was prepared in a similar fashion as described in Example 3.2, starting from 5-(4-(2-((tert-butoxycarbonylamino)methyl)-5-fluorobenzamido)-N-methylbutylsulfonamido)-8-(tosyloxy)-1,6-naphthyridine-7-carboxylic acid (Example 3.4; 1.1 mmol).

Example 3.6

Macrocyclization

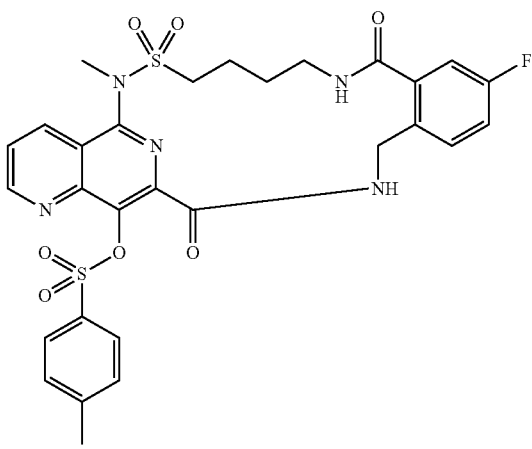 [SMILES: Cc1ccc(S(=O)(=O)Oc2c3nc(c4cccnc24)N(C)S(=O)(=O)CCCCNC(=O)c2cc(F)ccc2CNC3=O)cc1]

The target compound was prepared in a similar fashion as described in Example 1.6, starting from 5-(4-(2-(aminomethyl)-5-fluorobenzamido)-N-methylbutylsulfonamido)-8-(tosyloxy)-1,6-naphthyridine-7-carboxylic acid, TFA salt (Example 3.5; 1.57 mmol). The crude product was not purified and immediately used in the deprotection step (Compound 7).

Example 4.1

Methyl 8-(benzyloxy)-5-(4-(4-(tert-butoxycarbonylamino)butyl)-piperazin-1-yl)-1,6-naphthyridine-7-carboxylate

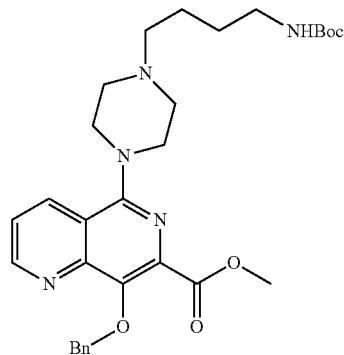 [SMILES: COC(=O)c1nc(N2CCN(CCCCNC(=O)OC(C)(C)C)CC2)c2cccnc2c1OCc1ccccc1]

To a solution of methyl 8-(benzyloxy)-5-(piperazin-1-yl)-1,6-naphthyridine-7-carboxylate (Example 13; 1.3 mmol) in DMA (10 ml) was added potassium carbonate (2.6 mmol), followed by tent-butyl 4-bromobutylcarbamate (1.3 mmol), and the reaction was stirred at r.t for 12 hr. Water and ethyl acetate were added. The combined organic layer was washed with water, dried over MgSO$_4$, filtered and concentrated, to afford the crude target compound (0.89 g).

Example 4.2

8-(Benzyloxy)-5-(4-(4-(tert-butoxycarbonylamino)butyl)piperazin-1-yl)-1,6-naphthyridine-7-carboxylic acid

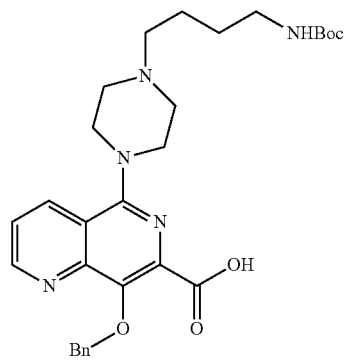 [SMILES: CC(C)(C)OC(=O)NCCCCN1CCN(c2nc(C(=O)O)c(OCc3ccccc3)c3ncccc23)CC1]

To a solution of methyl 8-(benzyloxy)-5-(4-(4-(tert-butoxycarbonylamino)butyl)-piperazin-1-yl)-1,6-naphthyridine-7-carboxylate (Example 4.1; 1.2 mmol) in a mixtire of methanol (2.5 ml) and water (2.5 ml) was added sodium hydroxide (2.5 mmol). The reaction mixture was stied at r.t. for 4 hr. The mixture was quenched with water and 2N HCl until pH=6 was reached. The mixture was extracted with AcOEt (2×). The organic layer was dried (MgSO₄), and filtered to afford a solid (400 mg), that was used as such in the next step.

Example 4.3

Ethyl 2-((8-(benzyloxy)-5-(4-(4-(tert-butoxycarbonylamino)butyl)-piperazin-1-yl)-1,6-naphthyridine-7-carboxamido)methyl)-5-fluorobenzoate

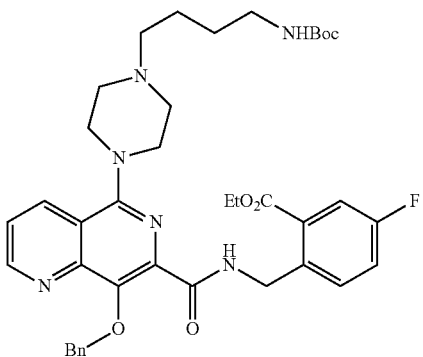 [SMILES: CCOC(=O)c1cc(F)ccc1CNC(=O)c1nc(N2CCN(CCCCNC(=O)OC(C)(C)C)CC2)c2cccnc2c1OCc1ccccc1]

8-(Benzyloxy)-5-(4-(4-(tert-butoxycarbonylamino)butyl)piperazin-1-yl)-1,6-naphthyridine-7-carboxylic acid (Example 4.2; 1.4 mmol) was dissolved in dichloro methane (14 ml). DIPEA (5.4 mmol) and HBTU (1.6 mmol) were added. The reaction mixture was stirred at room temperature during 5 min. Ethyl 2-(aminomethyl)-5-fluorobenzoate hydrochloride (Example 4; 1.6 mmol) was added portionwise at room temperature. The mixture was stirred overnight at room temperature. The mixture was diluted with CH₂Cl₂ and washed with a saturated aqueous Na₂CO₃ solution (2×) and H₂O. The organic layer was separated, dried (MgSO₄), filtered and evaporated. The residue was purified by flash column chromatography over silica gel (eluent: hexane/EtOAc 10:1 up to 1:1) to afford 0.97 gr of the title compound.

Example 4.4

2-((8-(Benzyloxy)-5-(4-(4-(tert-butoxycarbonylamino)butyl)piperazin-1-yl)-1,6-naphthyridine-7-carboxamido)methyl)-5-fluorobenzoic acid

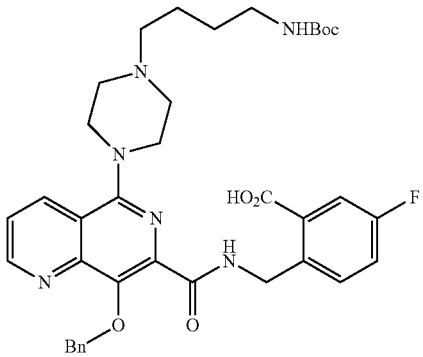 [SMILES: CC(C)(C)OC(=O)NCCCCN1CCN(c2nc(C(=O)NCc3ccc(F)cc3C(=O)O)c(OCc3ccccc3)c3ncccc23)CC1]

Ethyl 2-((8-(benzyloxy)-5-(4-(4-(tert-butoxycarbonylamino)butyl)piperazin-1-yl)-1,6-naphthyridine-7-carboxamido)methyl)-5-fluorobenzoate (Example 4.3; 1.4 mmol) was dissolved in THF (4.5 ml) and water (4.5 ml). Solid LiOH hydrate (1.6 mmol) was added at room temperature. The reaction mixture was stirred for 24 h, after which 2N HCl was added until pH=6-7 was reached. The mixture was extracted twice with EtOAc and the combined organic fractions dried with magnesium sulfate. The crude material containing the title compound (0.27 gr) was used as such in the next step.

Example 4.5

2-((5-(4-(4-aminobutyl)piperazin-1-yl)-8-hydroxy-1,6-naphthyridine-7-carboxamido)methyl)-5-fluorobenzoic acid, TFA salt

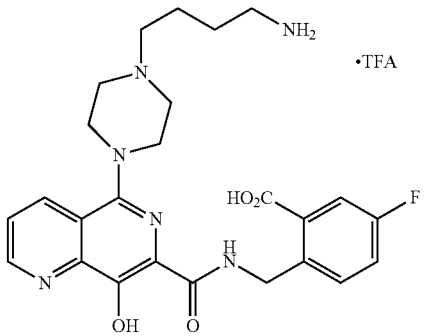 [SMILES: NCCCCN1CCN(c2nc(C(=O)NCc3ccc(F)cc3C(=O)O)c(O)c3ncccc23)CC1]

2-((8-(Benzyloxy)-5-(4-(4-(tert-butoxycarbonylamino)butyl)piperazin-1-yl)-1,6-naphthyridine-7-carboxamido)methyl)-5-fluorobenzoic acid (Example 4.4; 0.39 mmol) was dissolved in dichloromethane (1.6 ml), and cooled to 0° C. A mixture of TFA (1.6 ml) and dichloro methane (1.6 ml) was added to this cold solution, and the reaction mixture was stirred and gradually warmed from 0° C. to room temperature during 1 hour. The solvent was evaporated under reduced pressure and the residue was distilled azeotropically with toluene (2×). The resulting residue (0.42 g) was dried under high-vacuum and used in the next step (Compound 8) without further purification.

Example 5.1

Methyl 8-(benzyloxy)-5-(4-(5-(2-((tert-butoxycarbonylamino)methyl)-5-fluorophenoxy)pentanoyl)piperazin-1-yl)-1,6-naphthyridine-7-carboxylate

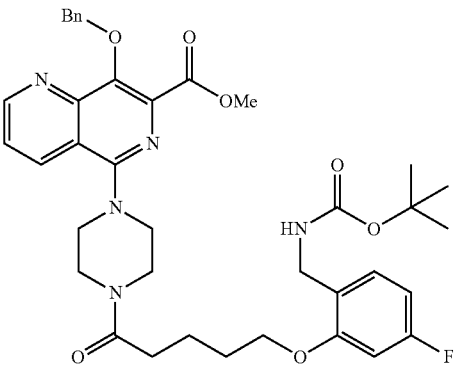 [SMILES: COC(=O)c1nc(N2CCN(C(=O)CCCCOc3cc(F)ccc3CNC(=O)OC(C)(C)C)CC2)c2cccnc2c1OCc1ccccc1]

To a solution of methyl 8-(benzyloxy)-5-(piperazin-1-yl)-1,6-naphthyridine-7-carboxylate (Example 13; 1.3 mmol), 5-(2-((tert-butoxycarbonylamino)methyl)-5-fluorophenoxy)pentanoic acid (Example 17; 1.6 mmol) and diisopropyl ethylamine (3.9 mmol) in dichloromethane (10 ml) was added HBTU (2.0 mmol). The mixture was stirred overnight. The mixture was washed with saturated NaHCO₃, 10% citric acid and brine and dried over Na₂SO₄. The solvent was removed under vacuum. The residue was purified by flash column chromatography over SiO₂ (eluent: methanol/CH₂Cl₂, 1:100) to afford the title compound (800 mg).

Example 5.2

8-(Benzyloxy)-5-(4-(5-(2-((tert-butoxycarbonylamino)methyl)-5-fluorophenoxy)pentanoyl)piperazin-1-yl)-1,6-naphthyridine-7-carboxylic acid

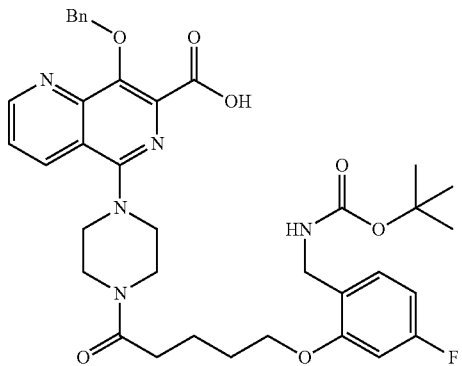 [SMILES: CC(C)(C)OC(=O)NCc1ccc(F)cc1OCCCCC(=O)N1CCN(c2nc(C(=O)O)c(OCc3ccccc3)c3ncccc23)CC1]

Methyl 8-(benzyloxy)-5-(4-(5-(2-((tert-butoxycarbonylamino)methyl)-5-fluorophenoxy)pentanoyl)piperazin-1-yl)-1,6-naphthyridine-7-carboxylate (Example 5.1; 1.1 mmol) was dissolved in a mixture of THF (6 ml), methanol (6 ml) and water (6 ml). Sodium hydroxide (7.5 mmol) was added and stirred for 2 days. The organic solvent was removed under vacuum, and the residue washed with diethyl ether. The aqueous residue was acidified with 1 N HCl to pH=8-9. The mixture was washed with ethyl acetate. The aqueous phase was acidified with 1N HCl to pH 3-4. The mixture was extracted with ethyl acetate and the organic layer was washed with brine and dried over Na₂SO₄. The solvent was removed under vacuum to afford the title compound (0.4 gr) that was used as such in the next step.

Example 5.3

5-(4-(5-(2-(Aminomethyl)-5-fluorophenoxy)pentanoyl)piperazin-1-yl)-8-(benzyloxy)-1,6-naphthyridine-7-carboxylic acid, TFA salt

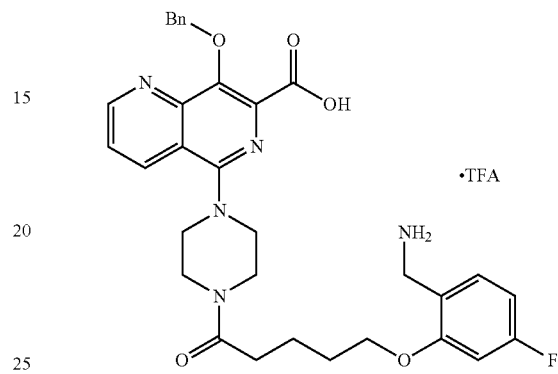

The title compound was prepared in a similar way as described in Example 1.5, from 8-(benzyloxy)-5-(4-(5-(2-((tert-butoxycarbonylamino)methyl)-5-fluorophenoxy)-pentanoyl)piperazin-1-yl)-1,6-naphthyridine-7-carboxylic acid (Example 5.2)

Example 5.4

Macrocyclization of 5-(4-(5-(2-(Aminomethyl)-5-fluorophenoxy)-pentanoyl)piperazin-1-yl)-8-(benzyloxy)-1,6-naphthyridine-7-carboxylic acid, TFA salt

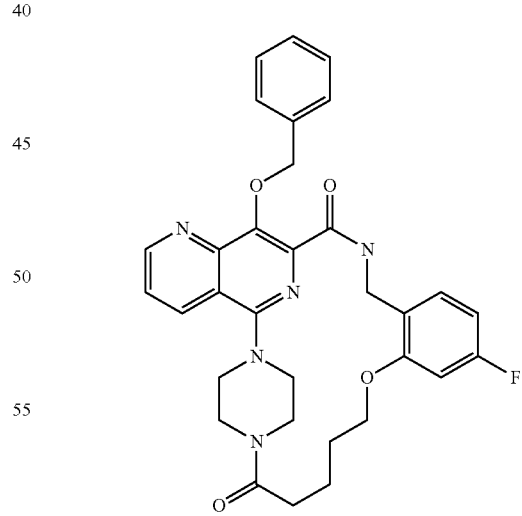

A solution of 5-(4-(5-(2-(aminomethyl)-5-fluorophenoxy)pentanoyl)piperazin-1-yl)-8-(benzyloxy)-1,6-naphthyridine-7-carboxylic acid, TFA salt (Example 5.3; 0.59 mmol) and diisopropyl ethylamine (1.8 mmol) in DMF (20 ml) was added dropwise to a mixture of pentafluorophenyl diphenylphosphinate (0.71 mmol) and diisopropyl ethylamine (0.4 ml) in diisopropyl ethylamine (1.8 mmol) in DMF (140 ml)

for 30 min. The mixture was stirred for 36 h at room temperature. The solvent was removed under vacuum and the residue was dissolved in CH₂Cl₂, washed with saturated NaHCO₃, 10% citric acid, saturated NaHCO₃ and brine and dried over Na₂SO₄. The solvent was removed under vacuum, and the solid residue was washed with ether to afford 300 mg as a powder that was used as such in the next step (Compound 10).

Example 6.1

Methyl 5-(4-(2-((tert-butoxycarbonylamino)methyl)-5-fluorophenoxy)-N-methylbutylsulfonamido)-8-methoxy-1,6-naphthyridine-7-carboxylate

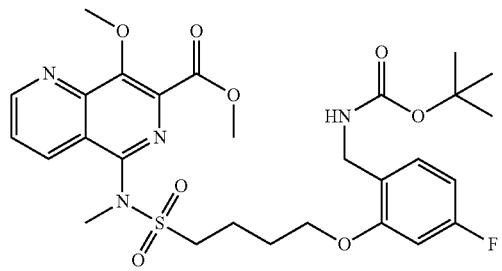 [SMILES: COC(=O)c1nc(N(C)S(=O)(=O)CCCCOc2cc(F)ccc2CNC(=O)OC(C)(C)C)c2cccnc2c1OC]

A mixture of methyl 5-bromo-8-methoxy-1,6-naphthyridine-7-carboxylate (2.4 mmol), tert-butyl 4-fluoro-2-(4-(N-methylsulfamoyl)butoxy)benzylcarbamate (Example 19; 2.6 mmol), 2,2'-bipyridine (3.1 mmol) and copper (I) oxide (3.1 mmol) in NMP (30 ml) was stirred at 120° C. under nitrogen atmosphere for 10 hours. The reaction mixture was diluted with dichloromethane and filtered off. The filtrate was washed with 10% 2-[2-(bis(carboxylatomethyl)amino)ethyl-(carboxylatomethyl)amino]acetate (EDTA) disodium salt solution, saturated NaHCO₃ solution and brine.

The organic layer was concentrated in vacuo and then methyl t-butyl ether was added. The mixture was washed with brine and the organic layer was dried over MgSO₄, filtered off and concentrated in vacuo to give the crude product.

The crude product was purified by flash column chromatography on SiO₂ (eluent: petroleum ether/ethyl acetate from 100/0 to 60/40) to give the title compound (0.48 g, 30% yield.

Example 6.2

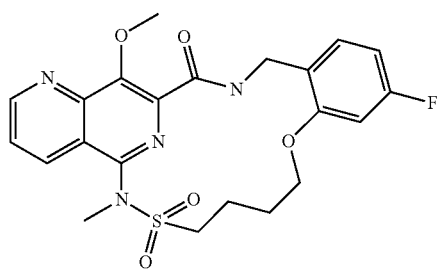 [SMILES: COc1c2nc(c3cccnc13)N(C)S(=O)(=O)CCCCOc1cc(F)ccc1CNC2=O]

The title compound was prepared in a 3 step process from methyl 5-(4-(2-((tert-butoxycarbonylamino)methyl)-5-fluorophenoxy)-N-methylbutylsulfonamido)-8-methoxy-1,6-naphthyridine-7-carboxylate (Example 6.1) following similar procedures as described in Examples 5.2; 5.3 and 5.4.

Example 7.1

Methyl 5-(5-(2-((tert-butoxycarbonylamino)methyl)-5-fluorophenoxy)-N-methylpentylsulfonamido)-8-methoxy-1,6-naphthyridine-7-carboxylate

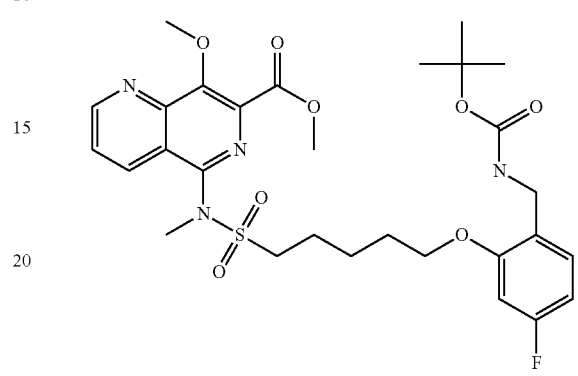

The title compound was prepared in a similar way as described for Example 6.1, using tert-butyl 4-fluoro-2-(5-(N-methylsulfamoyl)pentyloxy)benzylcarbamate (Example 23) and 5-bromo-8-methoxy-1,6-naphthyridine-7-carboxylate.

Example 7.2

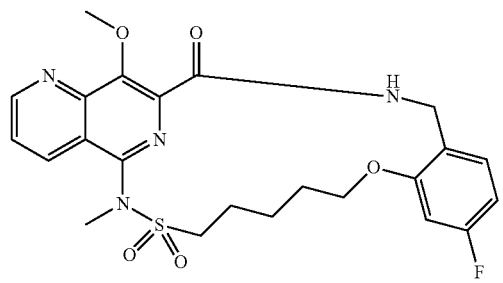 [SMILES: COc1c2nc(c3cccnc13)N(C)S(=O)(=O)CCCCCOc1cc(F)ccc1CNC2=O]

The title compound was prepared in a 3 step process from methyl 5-(5-(2-((tert-butoxycarbonylamino)methyl)-5-fluorophenoxy)-N-methylpentylsulfonamido)-8-methoxy-1,6-naphthyridine-7-carboxylate (Example 7.1) following similar procedures as described in Examples 5.2; 5.3 and 5.4.

Compound 1

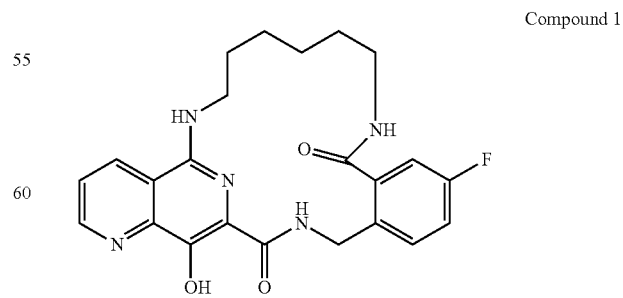

The macrocycle from Example 1.6 (80 mg; 0.15 mmol) was dissolved in 4N HCl in 1,4-dioxane (5 ml) and the mixture was heated at 40° C. for 1 hour. The reaction mixture was concentrated under vacuum. The residue was triturated from methanol and the solid product was filtered off and dried.

Yield: 0.055 g (99%; HPLC purity: 96%), isolated as HCl salt $^1$H NMR (400 MHz, DMSO-$d_6$) δ ppm 1.25-1.65 (m, 8H) 3.44 (br. s., 4H) 4.70 (d, J=5.3 Hz, 2H) 7.58 (br. s., 1H) 7.36 (t, J=7.3 Hz, 1H) 7.59 (t, J=6.5 Hz, 1H) 7.64 (d, J=9.0 Hz, 1H) 7.81 (br. s., 1H) 8.73 (t, J=5.3 Hz, 1H) 8.90 (d, J=7.2 Hz, 1H) 9.05 (br. s., 1H) 9.48 (t, J=5.3 Hz, 1H) 12.48 (br. s., 1H)

solvent was evaporated. The residue was triturated from diethyl ether, the product was collected by filtration and dried.

Yield: 0.023 g as a solid (32%; HPLC purity: 97%)

$^1$H NMR (400 MHz, DMSO-$d_6$) δ ppm 1.98 (br. s., 2H) 3.34 (br. s., 2H) 3.40 (br. s., 2H) 4.78 (d, J=4.5 Hz, 2H) 7.31 (t, J=7.5 Hz, 1H) 7.39 (d, J=8.6 Hz, 1H) 7.55 (t, J=6.3 Hz, 1H) 7.69 (dd, J=7.2, 3.7 Hz, 1H) 7.73 (br. s., 1H) 8.56-8.72 (m, 2H) 9.03 (d, J=3.7 Hz, 1H) 9.10 (t, J=5.5 Hz, 1H) 11.69 (br. s., 1H)

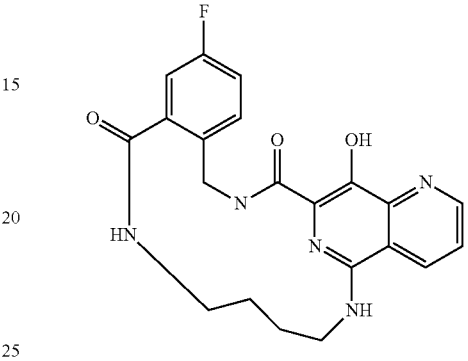

Compound 3

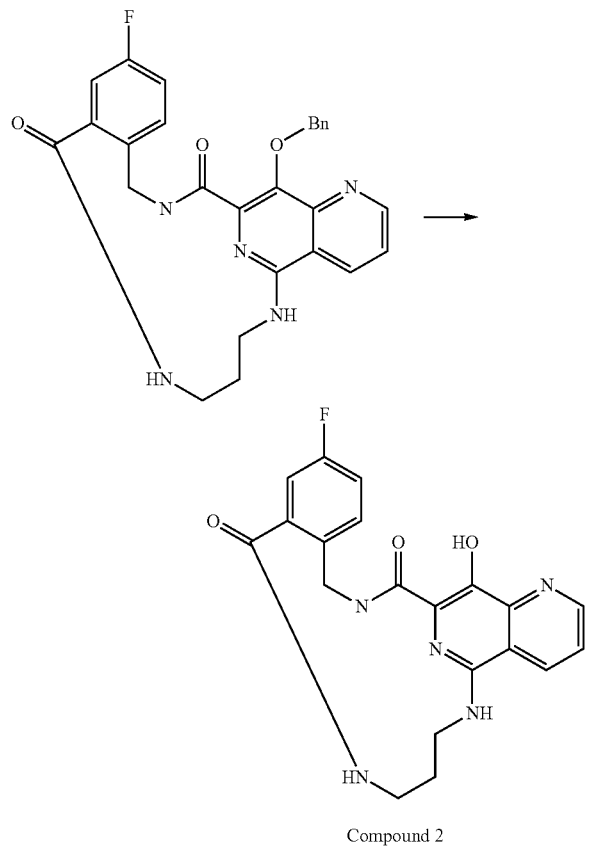

Compound 2

Compound 2

The O-benzyl protected precursor of compound 2 was prepared in an analogous fashion as described for Examples 1.1-1.6, starting from methyl 8-(benzyloxy)-5-bromo-1,6-naphthyridine-7-carboxylate (Example 1) and N-tert-butoxycarbonyl-1,3-diamino-propane. De-benzylation to obtain compound 2 was carried out as follows. The O-benzyl precursor macrocycle was dissolved in dichloro methane (3.6 ml) and cooled to 0° C. To this mixture was added a freshly prepared solution, consisting of trifluoro acetic acid (3.6 ml), triisopropyl silane (0.075 ml) and dichloro methane (3.6 ml). The ensuing mixture was allowed to warm to room temperature over 1 h The reaction mixture was concentrated under vacuum. The residue was dissolved in dichloro methane, and washed with satd. NaHCO$_3$. The aqueous phase was extracted with dichloro methane (2×). The combined organic layers were dried (MgSO$_4$), filtered and the solvent was evaporated. The crude material was purified by flash column chromatography over silica gel (eluent: CH$_2$Cl$_2$/MeOH from 50:1 up to 10:1). The product fractions were collected and the This compound was prepared in an analogous fashion as described for Examples 1.1-1.6 and Compound 2, starting from methyl 8-(benzyloxy)-5-bromo-1,6-naphthyridine-7-carboxylate (Example 1) and N-tert-butoxycarbonyl-1,3-diaminobutane. The resulting compound was characterized by reversed phase HPLC using an Agilent 1100 series liquid chromatography system comprising a binary pump with degasser, an autosampler, a column oven and a UV detector, with a YMC-Pack ODS-AQ C18 column (4.6×50 mm). The column temperature was 35° C. The mobile phase was maintained at a flow rate of 2.6 ml/min with a gradient going from 95% water and 5% acetonitrile to 95% acetonitrile in 4.80 minutes and the latter held for 1.20 minutes. Flow from the column was split to a MS spectrometer. The MS detector was configured with an electrospray ionization source. The capillary voltage was 3 kV, the quadrupole temperature was maintained at 100° C. and the desolvation temperature was 300° C. Nitrogen was used as the nebulizer gas. Mass spectra were acquired by scanning from 100 to 1400. Injection volume was 10 μl. Data acquisition was performed with an Agilent Chemstation data system. Rt: 2.6 min.; MH$^+$: 410

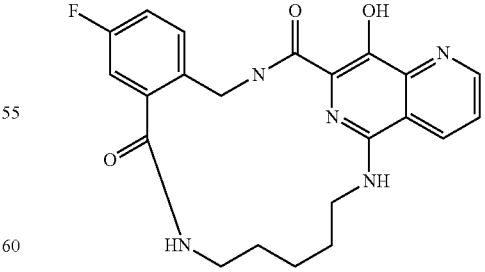

Compound 4

This compound was prepared in an analogous fashion as described for Examples 1.1-1.6 and Compound 1, and was isolated as a HCL salt, starting from methyl 8-(benzyloxy)-5-bromo-1,6-naphthyridine-7-carboxylate (Example 1) and N-tert-butoxycarbonyl-1,3-diaminopentane.

$^1$H NMR (400 MHz, DMSO-d$_6$) δ ppm 1.45 (br. s., 4H) 1.64-1.76 (qt, J=5.7 Hz, 2H) 3.34 (q, J=5.5 Hz, 2H) 3.71 (t, J=5.3 Hz, 2H) 4.80 (d, J=6.6 Hz, 2H) 7.58 (br. s., 1H) 7.32 (t, J=7.4 Hz, 1H) 7.40 (d, J=9.2 Hz, 1H) 7.56 (t, J=6.8 Hz, 1H) 7.80 (dd, J=7.4, 4.3 Hz, 1H) 8.62 (t, J=5.5 Hz, 1H) 8.87 (t, J=6.6 Hz, 1H) 8.91 (d, J=7.4 Hz, 1H) 9.05 (d, J=4.3 Hz, 1H) 12.13 (br. s., 1H)

Compound 5

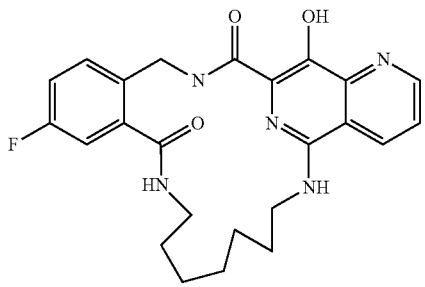

This compound was prepared in an analogous fashion as described for Examples 1.1-1.6 and Compound 1, starting from methyl 8-(benzyloxy)-5-bromo-1,6-naphthyridine-7-carboxylate (Example 1) and N-tert-butoxycarbonyl-1,3-diaminoheptane. Compound 5 was isolated as HCl salt. The resulting compound was characterized by reversed phase HPLC using the method described for compound 3. Rt: 3.3 min. MH$^+$: 452

Compound 6

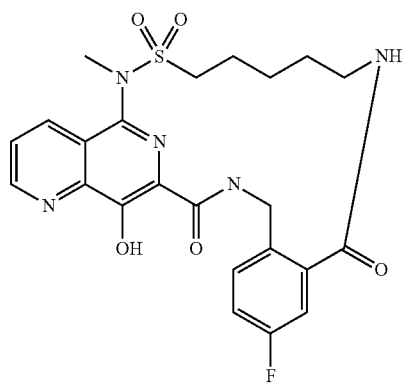

To a solution of 2-((5-(5-amino-N-methylpentylsulfonamido)-8-hydroxy-1,6-naphthyridine-7-carboxamido)methyl)-5-fluorobenzoic acid, HCl salt (Example 2.6; 1.94 mmol) in DMF (70 ml) was slowly added drop wise a solution of HBTU (5.77 mmol) and triethyl amine (58 mmol) in DMF (250 mL) at r.t. HPLC showed complete conversion. A solution of NH3 in methanol was added. The mixture was stirred for 30 min at r.t. The solvent was evaporated. The residue was purified by reverse chromatography to yield the target compound in 4% yield.

1H NMR (400 MHz, DMSO-d$_6$) δ ppm 1.38 (qt, J=6.7 Hz, 2H), 1.61 (qt, J=6.5 Hz, 2H), 1.89 (qt, J=7.2 Hz, 2H), 3.31-3.39 (m, 4H), 3.41 (s, 3H), 4.74 (d, J=6.1 Hz, 2H), 7.36 (td, J=8.6, 2.4 Hz, 1H), 7.48 (dd, J=9.7, 2.1 Hz, 1H), 7.68 (dd, J=8.2, 6.1 Hz, 1H), 7.87 (dd, J=8.4, 4.3 Hz, 1H), 8.58 (d, J=8.4 Hz, 1H), 8.70 (t, J=5.5 Hz, 1H), 9.17 (d, J=2.7 Hz, 1H), 9.64 (t, J=6.0 Hz, 1H), 13.65 (br. s., 1H)

Compound 7

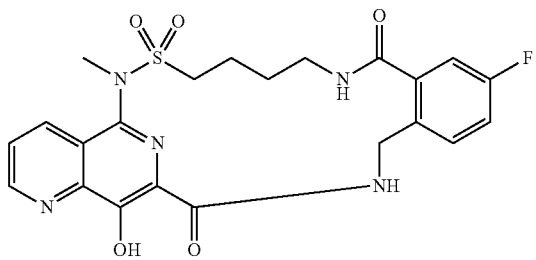

The crude macrocycle obtained in Example 3.6 (1.6 mmol) was dissolved in DMF (8 mL), and transferred to a 30% solution of NaOMe in methanol over ca 1-2 min at room temperature. The reaction mixture was quenched with acetic acid (3 mL), the solvent evaporated in vacuo, and the residue purified by reversed phase HPLC to afford the title compound in 14% yield over the last two steps.

1H NMR (400 MHz, DMSO-d$_6$) δ ppm 1.70 (quin, J=6.5 Hz, 2H) 1.80 (quin, J=7.5 Hz, 2H) 3.30-3.35 (m, 2H) 3.37 (s, 3H) 3.52 (br. s., 2H) 4.74 (d, J=5.6 Hz, 2H) 7.28-7.35 (m, 2H) 7.62 (dd, J=8.1, 5.8 Hz, 1H) 7.89 (dd, J=8.4, 4.1 Hz, 1H) 8.54 (dd, J=8.4, 1.1 Hz, 1H) 8.59 (t, J=5.2 Hz, 1H) 8.94 (t, J=5.6 Hz, 1H) 9.17 (dd, J=4.1, 1.1 Hz, 1H) 13.60 (br. s., 1H)

Compound 8

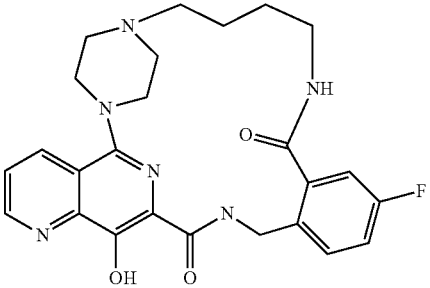

A solution of crude 2-((5-(4-(4-aminobutyl)piperazin-1-yl)-8-(hydroxy)-1,6-naphthyridine-7-carboxamido)methyl)-5-fluorobenzoic acid TFA salt (Example 4.5; 0.39 mmol) in DMF (40 ml) was slowly added to a solution of HBTU (1.2 mmol) and DIPEA (11.8 mmol) in DMF (90 ml) at room temperature over 4 hours. A 30% solution of ammonia (3 ml) was added to the reaction mixture and the volatiles removed in vacuo. The residue was partitioned between dichloromethane and a saturated aqueous NaHCO$_3$ solution (×2). The layers were separated. The organic layer was dried (MgSO$_4$), filtered and the solvent was evaporated. The crude material was purified by preparative HPLC to afford the target material as a powder (56 mg).

1H NMR (400 MHz, DMSO-d$_6$) δ ppm 1.42 (quin, J=6.6 Hz, 2H) 1.52 (quin, J=5.8 Hz, 2H) 2.47 (d, J=11.4 Hz, 2H) 2.70 (t, J=6.6 Hz, 2H) 2.89 (t, J=10.4 Hz, 2H) 3.34-3.44 (m, 4H) 3.70 (d, J=12.7 Hz, 2H) 4.79 (d, J=6.3 Hz, 2H) 7.39 (td, J=8.3, 2.5 Hz, 1H) 7.64-7.72 (m, 3H) 8.44 (dd, J=8.4, 1.1 Hz, 1H) 8.59 (t, J=5.6 Hz, 1H) 9.00 (t, J=6.3 Hz, 1H) 9.05 (dd, J=4.1, 1.1 Hz, 1H) 12.72 (br. s., 1H)

Compound 9

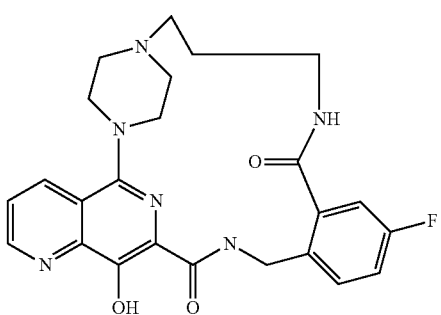

This compound was prepared in an analogous fashion as described for Examples 4.1-4.5 and Compound 8.

1H NMR (300 MHz, DMSO-d$_6$) δ ppm 1.56-1.68 (m, 2H) 2.43 (d, J=11.0 Hz, 2H) 2.63 (br. s., 2H) 2.79 (t, J=11.0 Hz, 2H) 3.36-3.55 (m, 4H) 3.71 (d, J=12.8 Hz, 2H) 4.89 (d, J=3.0 Hz, 2H) 7.37 (td, J=8.0, 2.5 Hz, 1H) 7.57-7.65 (m, 2H) 7.70 (dd, J=8.5, 4.1 Hz, 1H) 8.42 (d, J=8.5 Hz, 1H) 8.67-8.78 (m, 2H) 9.05 (d, J=4.1 Hz, 1H) 11.28 (br. s., 1H)

Compound 10

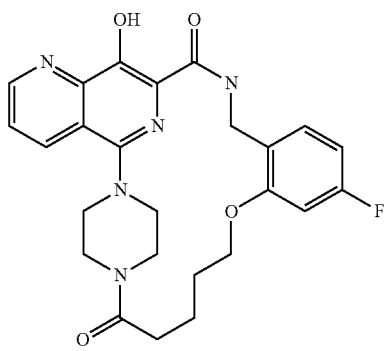

The protected macrocycle from Example 5.4 (0.2 gr) was dissolved in TFA (5 ml) and refluxed for 2 h. The solvent was removed under vacuum. The residue was triturated with saturated NaHCO$_3$ for 15 min., and the solid was collected by filtration. The precipitate was purified by prep. TLC (eluent: CH$_2$Cl$_2$/methanol, 10:1). The residue was purified by prep. HPLC (C18, eluent: MeOH/H$_2$O/TFA, 50:50:0.5). The collected fractions were combined, concentrated under vacuum, basified to pH=7-8 with saturated NaHCO$_3$ and extracted with CH$_2$Cl$_2$. The solvent was removed under vacuum, and the residue was recrystallized from CH$_3$CN to afford the title compound as a solid (6 mg).

1H NMR (400 MHz, CHLOROFORM-d) δ ppm 1.75-1.86 (m, 1H) 2.02-2.24 (m, 3H) 2.33-2.39 (m, 1H) 2.77-2.89 (m, 2H) 3.07 (dt, J=11.9, 2.8 Hz, 1H) 3.13-3.25 (m, 2H) 3.61-3.69 (m, 1H) 3.76-3.84 (m, 1H) 3.97-4.04 (m, 1H) 4.10-4.16 (m, 1H) 4.18-4.24 (m, 1H) 4.53 (dd, J=14.2, 6.8 Hz, 1H) 4.59-4.65 (m, 1H) 4.67 (dd, J=14.2, 6.8 Hz, 1H) 6.61-6.67 (m, 2H) 7.32 (t, J=7.2 Hz, 1H) 7.61 (dd, J=8.4, 4.2 Hz, 1H) 8.60 (dd, J=8.4, 1.6 Hz, 1H) 8.67 (t, J=6.8 Hz, 1H) 9.13 (dd, J=4.2, 1.6 Hz, 1H) 12.82 (s, 1H)

Compound 11

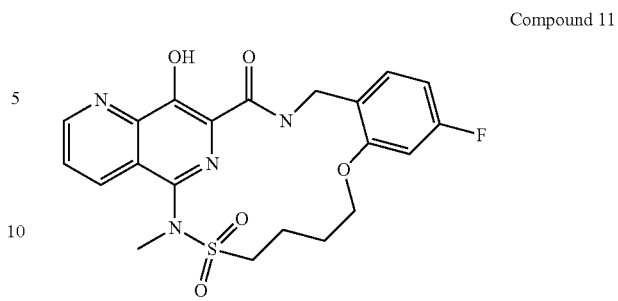

To a solution of the macrocyle obtained in Example 6.2 (0.42 mmol) and sodium iodide (0.92 mmol) in acetonitrile (2 ml) and toluene (2 ml) was added SiCl$_4$ (0.92 mmol)) at 0° C. under nitrogen atmosphere. After completion of the reaction, water (10 ml) and methanol (10 ml) were added, followed by extraction with CH$_2$Cl$_2$ (3*10 ml). The combined organic layers were washed with brine (15 ml) and dried over Na$_2$SO$_4$, filtered and evaporated under reduced pressure.

The residue was washed with ethyl ether and CH$_3$CN. The title compound was obtained by filtration (42 mg).

1H NMR (400 MHz, CHLOROFORM-d) δ ppm 2.04 (br. s., 2H) 2.46 (br. s., 2H) 3.38-3.45 (m, 5H) 4.08 (br. s., 2H) 4.61 (d, J=5.5 Hz, 2H) 6.59-6.72 (m, 2H) 7.34 (t, J=7.0 Hz, 1H) 7.70 (dd, J=8.0, 4.3 Hz, 1H) 8.63 (d, J=8.0 Hz, 2H) 9.18 (br. s., 1H) 13.33 (s, 1H)

Compound 12

This compound was prepared in an analogous fashion as described in Compound 11, using Example 7.2 as the starting material.

1H NMR (400 MHz, CHLOROFORM-d) δ ppm 1.83 (quin, J=7.2 Hz, 2H) 2.05 (quin, J=5.7 Hz, 2H) 2.21 (br. s., 2H) 3.31 (t, J=8.0 Hz, 2H) 3.41 (s, 3H) 4.19 (t, J=4.8 Hz, 2H) 4.66 (d, J=6.0 Hz, 2H) 6.63-6.73 (m, 2H) 7.34 (t, J=7.1 Hz, 1H) 7.69 (dd, J=8.3, 4.0 Hz, 1H) 8.29 (t, J=6.0 Hz, 1H) 8.63 (d, J=8.3 Hz, 1H) 9.18 (d, J=4.0 Hz, 1H) 13.58 (s, 1H)

B. Biological Activity of Compounds of Formula I

Assay 1—Inhibitory Activity on HIV Replication Wild Type, N155H Mutant, and Q148R Mutant MT4-LTR-enhanced green fluorescent protein (EGFP) cells were obtained by transfecting MT4 cells with a selectable construct encompassing the coding sequences for the HIV LTR as a promoter for the expression of EGFP and subsequent selection of permanently transfected cells. MT4-cytomegalovirus (CMV)-EGFP cells were obtained by selection for permanently transformed MT4 cells with a CMV-EGFP reporter gene. Cell lines were maintained in RPMI 1640 medium supplemented with 10% heat-inactivated fetal calf serum, 2 mM L-glutamine, 0.1% NaHCO$_3$, and antibiotics (0.02% gentamicin and 0.8% G418) and incubated in a humidified incubator with a 5% CO$_2$ atmosphere at 37° C.

N155H and Q148R mutant Integrase coding sequences were constructed in the pUC19-5'HXB2D vector (XbaI-SalI fragment of pHXB2D), containing the HIV-1 clone HXB2D IN coding sequence, by using a QuikChange site-directed mutagenesis kit (Stratagene, La Jolla, Calif.) and high-performance liquid chromatography-purified primers (Genset Oligos, La Jolla, Calif.). Altered plasmid sequences were confirmed by dideoxyribose sequencing.

For generation of site directed mutant (SDM) virus stocks, MT4 cells were subcultured at a density of 250,000 cells/ml on the day before transfection. Cells were pelleted and resuspended in phosphate-buffered saline at a concentration of 3.1×106 cells/ml. A 0.8-ml portion (2.5×106 cells/ml) was used for each transfection. Transfections were performed with a Bio-Rad Gene Pulser (Bio-Rad, Hercules, Calif.) with 0.4-cm electrode cuvettes (Bio-Rad). Cells were electroporated with 10 µg of SalI-linearized pUC19-3'HXB2D (SalI-XbaI fragment of pHXB2D) and 5 µg of SalI-digested SDM at 250 µF and 300 V, followed by a 30-min incubation at room temperature. Ten milliliters of fresh culture medium was then added to the suspension of transfected cells, and incubation was performed at 37° C. in a humidified atmosphere with 5% CO$_2$. Cell cultures were monitored for the appearance of cytopathic effect (CPE). At virus breakthrough (full CPE), culture supernatant was typically harvested by centrifugation at 8 to 10 days after transfection and was stored at −80° C. for subsequent drug susceptibility determination.

The antiviral activity of different inhibitors was determined in a cell-based HIV-1 replication assay. MT4-LTR-EGFP cells (150,000 cells/ml) were infected with HIV-1 (IIIB or site-directed mutant strains N155H or Q148R; multiplicity of infection [MOI] of 0.0025) in the presence or absence of inhibitor. After 3 days of incubation, the inhibition of HIV replication was quantified by measuring EGFP fluorescence, and expressed as the inhibitor concentration required for 50% inhibition of HIV-1 replication in cell culture (IIIB EC50—see Table 1).

Assay 2—Cellular Cytotoxic Activity

The cytotoxicity of inhibitors was determined in parallel to the experiments under assay 1 on mock-infected MT4-CMV-EGFP cells (150,000 cells/ml) cultured in the presence or absence of different concentrations of compounds of formula I. After 3 days of incubation, inhibition of cell proliferation was quantified by measuring the EGFP fluorescence and expressed as the compound concentration that inhibits cell growth by 50% (CC$_{50}$—see Table 1).

Assay 3—Inhibitory Activity on HIV Replication Wild Type in the Presence of Human Serum For the Antiviral assay in the presence of 50% human serum MT-4-LTR-EGFP cells were infected with HIV-1 LAI (IIIB) at a MOI of 0.001 to 0.01 CCID50/cell in RPMI1640 medium. Following 1 h of incubation, cells were washed and plated into a 96-well plate containing serial dilutions of compound in the presence of 10% fetal calf serum (FCS), or 50% human serum. After 4 days incubation, the EC$_{50}$ in the presence of 50% human serum (EC$_{50}$/HS—see Table 1) was determined by a cell viability assay using resazurin (as described by Fields, R. D., and M. V. Lancaster (1993) Am. Biotechnol. Lab. 11:48-50).

Assay 4—3dQ Assay

The inhibition of HIV integrase mediated 3'-processing was determined in a biochemical assay. For this a short (~20 bp) double stranded U5 LTR substrate was generated by hybridization of 5 µM 5'-TGTGGAAAATCTCTAGCAGT-3'-alx488 (SEQ ID 1) with 7 µM dabcyl-5'-ACTGCTA-GAGATTTTCCACA-3' (SEQ ID 2) in 10 mM Tris pH 8.0, 100 mM NaCl (heating to 95° C. and gradually cooling over 30' to RT). Integrase inhibition was determined by incubation of 150 nM recombinant HIV-1 integrase, 100 nM recombinant LEDGF and 50 nM U5 LTR substrate in reaction buffer (25 mM MOPS pH7.2, 10 mM DTT, 10 mM MgCl$_2$, 15 mM potassium glutamate and 2.5% DMSO) in the presence or absence of different concentrations test compounds. After 2 h at 37° C. reactions were stopped by adding ⅓ volumes of 0.5% SDS and fluorescence was measured (excitation at 488 nm, emission at 538 nm) and expressed as the inhibitor concentration required for 50% inhibition of the HIV integrase (IC$_{50}$—see Table 1).

TABLE 1 biological activity against HIV replication

| example | IC$_{50}$ (µM) | IIIB.EC$_{50}$ (µM) | CC$_{50}$ (µM) | N155H EC$_{50}$ (µM) | Q148R EC$_{50}$ (µM) | EC$_{50}$/HS (µM) |
|---|---|---|---|---|---|---|
| 1 | 0.95 | 0.017 | 20.7 | 0.42 | 0.35 | 0.035 |
| 2 | 68 | 8.9 | 61 | | 36.7 | |
| 3 | | 1.06 | >98 | | 28.0 | |
| 4 | | 0.071 | >31 | 1.9 | 7.2 | 0.13 |
| 5 | 1.0 | 0.017 | 7.7 | 0.39 | 0.44 | 0.051 |
| 6 | 0.25 | 0.004 | 27.7 | 0.083 | 0.008 | 0.003 |
| 7 | 0.36 | 0.004 | 13.3 | 0.26 | 0.020 | 0.003 |
| 8 | 1.2 | 0.018 | 3.1 | 1.9 | 0.85 | 0.018 |
| 9 | 1.6 | 0.017 | 43 | 1.51 | 0.46 | 0.025 |
| 10 | | 0.003 | >24 | 0.11 | 0.039 | 0.027 |
| 11 | | 0.005 | >24 | 0.31 | 0.024 | 0.016 |
| 12 | 0.20 | 0.001 | >98 | 0.17 | 0.012 | 0.04 |

The invention claimed is:

1. A compound having formula (I)

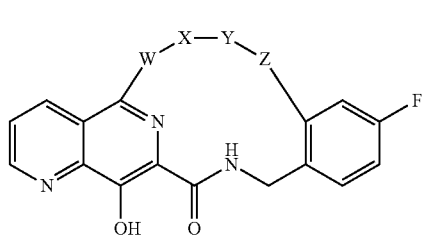
(I)

or a pharmaceutically acceptable salt thereof, wherein

W is —NH—, —N(CH$_3$)— or piperazine,

X is a bond, —C(=O)— or —S(=O)$_2$—,

Y is C$_{3-7}$alkylene, and

Z is —NH—C(=O)— or —O—.

2. The compound according to claim 1 wherein W is —NH— or —N(CH$_3$)—.

3. The compound according to claim 1 wherein X is a bond or —S(=O)$_2$—.

4. The compound according to claim 1 wherein Y is C$_{4-5}$alkylene.

5. The compound according to claim 1 wherein X is —C(=O)— and Y is C$_{3-4}$alkyl when W is piperazine.

6. The compound according to claim 1 wherein Z is —O—.

7. The compound according to claim 1 wherein Z is —NH—C(=O)—, wherein the nitrogen of —NH—C(=O)— is connected to Y.

8. The compound according to claim 1 wherein the —W—X—Y—Z— linker is 8 or 9 atoms long.

9. The compound according to claim 1 wherein —W—X—Y—Z— is selected from

- - -NH—C$_{5-7}$alkylene-NH—C(=O)- - -,

- - -N(CH$_3$)—S(=O)$_2$—C$_{4-5}$alkylene-NH—C(=O)- - -,

- - -N(CH$_3$)—S(=O)$_2$—C$_{4-5}$alkylene-O- - -,

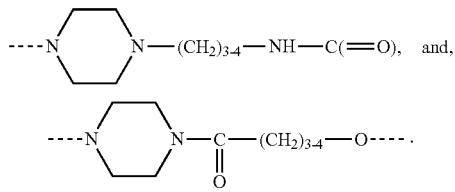

10. The compound of claim 1, or a pharmaceutically acceptable salt thereof, having the formula

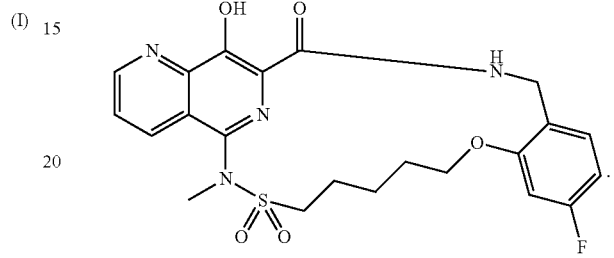

11. The compound of claim 1, or a pharmaceutically acceptable salt thereof, having the formula

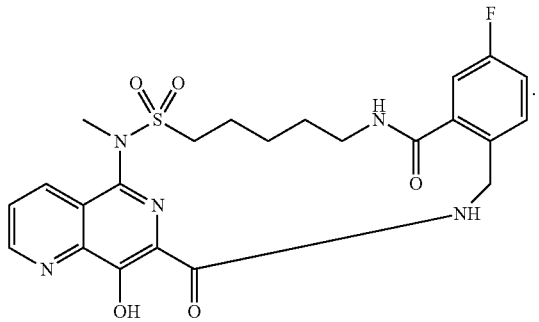 [SMILES: CN1c2nc(c(O)c3ncccc23)C(=O)NCc2ccc(F)cc2C(=O)NCCCCCS1(=O)=O]

12. The compound as claimed in claim 1, or a pharmaceutically acceptable salt thereof, having the formula:

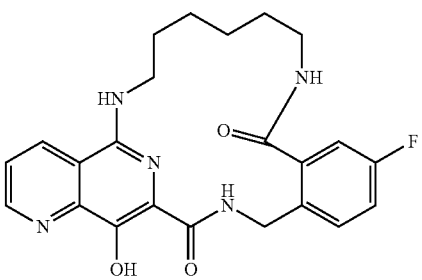

63
-continued
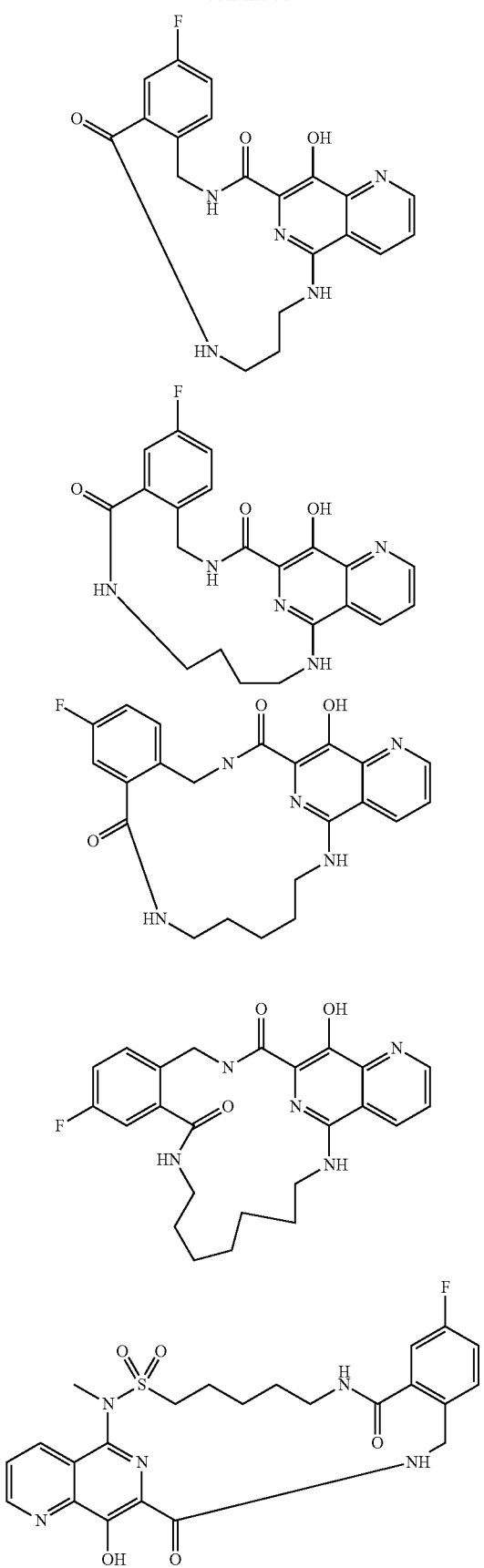
64
-continued
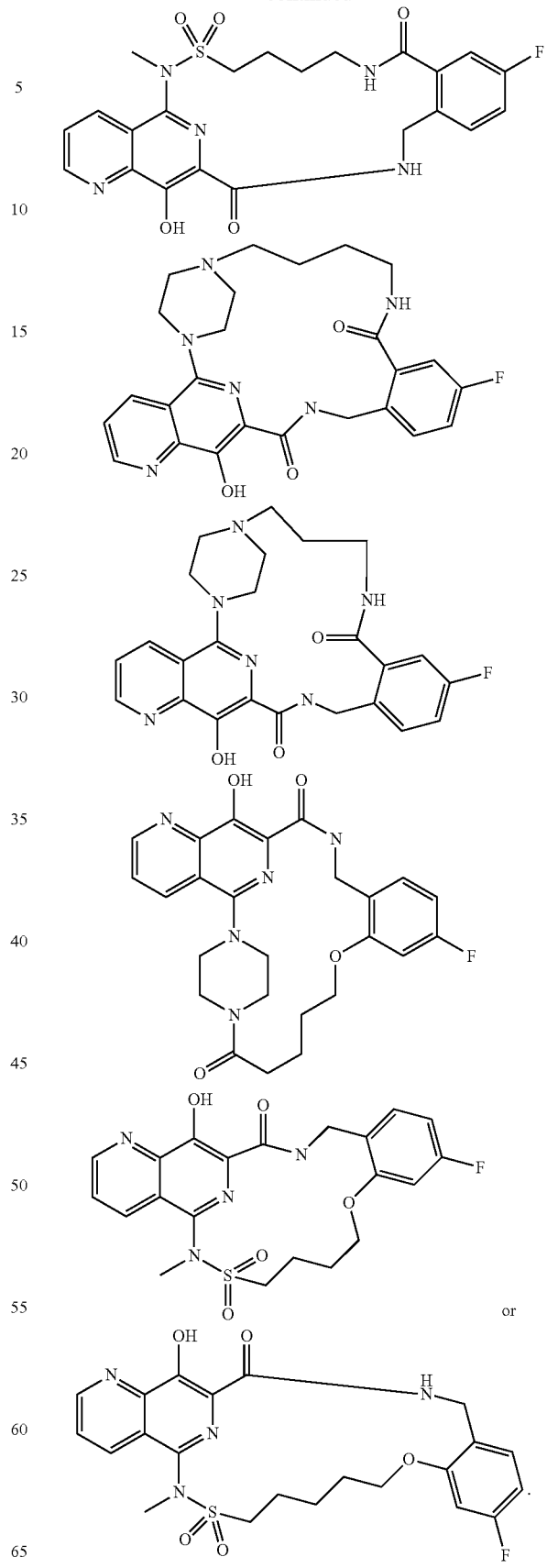
or

13. A pharmaceutical composition comprising a compound of formula (I) as defined in claim 1, and a carrier.

14. A pharmaceutical composition comprising a compound of formula (I) as defined in claim 12, and a carrier.

15. A method of inhibiting HIV replication in a patient in need thereof comprising administering a compound of claim 1 to said patient.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Human immunodeficiency virus

<400> SEQUENCE: 1
tgtggaaaat ctctagcagt                                           20

<210> SEQ ID NO 2
<211> LENGTH: 20

```
<212> TYPE: DNA
<213> ORGANISM: Human immunodeficiency virus

<400> SEQUENCE: 2
actgctagag attttccaca                                              20
```